US012416633B2

(12) United States Patent
Guzman

(10) Patent No.: US 12,416,633 B2
(45) Date of Patent: Sep. 16, 2025

(54) METHOD AND SYSTEM FOR EXPOSING HIDDEN OR MASKED ANTIGENIC SITES OF VIRAL SPECIMENS PRESENT IN BIOSAMPLES USING A HOME-BASED COVID-19 RAPID LATERAL FLOW IMMUNOASSAY TEST

(71) Applicant: PRINCETON BIOCHEMICALS, INC., Princeton, NJ (US)

(72) Inventor: Norberto A. Guzman, East Brunswick, NJ (US)

(73) Assignee: Princeton Biochemicals, Princeton, NJ (US)

( * ) Notice: Subject to any disclaimer, the term of this patent is extended or adjusted under 35 U.S.C. 154(b) by 68 days.

(21) Appl. No.: 18/088,996

(22) Filed: Dec. 27, 2022

(65) Prior Publication Data

US 2024/0210398 A1 Jun. 27, 2024

(51) Int. Cl.
*G01N 33/569* (2006.01)
*G01N 33/543* (2006.01)

(52) U.S. Cl.
CPC . *G01N 33/56983* (2013.01); *G01N 33/54388* (2021.08); *G01N 33/54393* (2013.01); *G01N 2333/165* (2013.01); *G01N 2469/10* (2013.01)

(58) Field of Classification Search
CPC ....... G01N 33/56983; G01N 33/54388; G01N 33/54393; G01N 2333/165; G01N 2469/10; G01N 33/558; G01N 33/54387; G01N 33/54389; B01L 2300/0825
USPC ....... 422/400, 401, 420, 421, 425, 426, 430; 435/287.7, 287.9, 970, 805; 436/170, 436/514, 518, 530, 810
See application file for complete search history.

(56) References Cited

U.S. PATENT DOCUMENTS 8,110,392 B2 2/2012 Battrell et al.
8,399,261 B2 3/2013 Kabir et al.
8,486,717 B2 7/2013 O'Farrell et al.
8,614,101 B2 12/2013 VanDine et al.
(Continued)

OTHER PUBLICATIONS

Wong, R. C. & Tse, H. Y. (2010). Lateral flow immunoassay. Springer (Year: 2010).*
(Continued)

*Primary Examiner* — Bao-Thuy L Nguyen
*Assistant Examiner* — Ellis Follett Lusi
(74) *Attorney, Agent, or Firm* — Calderone McKay, LLC

(57) ABSTRACT

A disease detection system including a platform or cartridge to perform testing using a rapid lateral flow chromatographic immunoassay (LFIA) test intended for the qualitative detection of the disease in a sample, such as collected sputum, disrupted by a digestive enzyme and a detergent to release its content and digest its proteins and other polymeric molecules. A method of the present invention includes treating a sample with a digestive enzyme and a detergent to disrupt the collected sample releasing content and digesting proteins of the sample to form a lysed-digested-extracted sample, applying the lysed-digested-extracted sample to a platform or cartridge, performing a rapid lateral flow chromatographic immunoassay (LFIA) test of the lysed-digested-extracted sample using the platform or cartridge and detecting presence or absence of an analyte of interest from the tested lysed-digested-extracted sample.

8 Claims, 16 Drawing Sheets

(56) References Cited

U.S. PATENT DOCUMENTS

| | | |
|---|---|---|
| 8,828,739 B2 | 9/2014 | Guo et al. |
| 8,900,850 B2 | 12/2014 | Lane et al. |
| 9,121,849 B2 | 9/2015 | Babu et al. |
| 9,146,234 B2 | 9/2015 | Guzman |
| 9,250,236 B2 | 2/2016 | Babu et al. |
| 9,314,479 B2 | 4/2016 | Nick et al. |
| 9,366,668 B2 | 6/2016 | Rao et al. |
| 9,482,602 B2 | 11/2016 | Guzman |
| 9,591,852 B2 | 3/2017 | Mordas et al. |
| 9,696,299 B2 | 7/2017 | Guzman |
| 9,933,423 B2 | 4/2018 | Sambursky et al. |
| 10,458,978 B2 | 10/2019 | Cary |
| 11,198,118 B2 | 12/2021 | Guzman et al. |
| 11,255,854 B2 | 2/2022 | Mehra et al. |
| 11,287,396 B2 | 3/2022 | Guzman |
| 11,307,198 B2 | 4/2022 | Lin et al. |
| 2004/0184954 A1 | 9/2004 | Guo et al. |
| 2006/0263907 A1 | 11/2006 | Zweig |
| 2007/0116750 A1 | 5/2007 | Wolcott |
| 2010/0099115 A1* | 4/2010 | Mach ............... G01N 33/56911 435/7.1 |
| 2015/0023086 A1 | 1/2015 | Messmer et al. |
| 2016/0320387 A1* | 11/2016 | Maehana ................. C12N 1/06 |
| 2019/0056391 A1 | 2/2019 | Deirmengian et al. |
| 2020/0033336 A1 | 1/2020 | Kamei et al. |
| 2020/0124593 A1 | 4/2020 | Oved et al. |
| 2021/0379580 A1 | 12/2021 | Sarhan et al. |
| 2022/0113307 A1* | 4/2022 | Cornell ............ G01N 33/54388 |
| 2022/0241772 A1 | 8/2022 | Fishlock et al. |
| 2023/0104815 A1* | 4/2023 | Mohanty .......... G01N 33/54346 435/5 |
| 2025/0001417 A1* | 1/2025 | Abbud-Antaki ... G01N 33/5308 |

OTHER PUBLICATIONS

Datta S, Christena LR, Rajaram YR. Enzyme immobilization: an overview on techniques and support materials. 3 Biotech. Feb. 2013 (Year: 2013).*

Folgueira L, Delgado R, Palenque E, Noriega AR. Detection of Mycobacterium tuberculosis DNA in clinical samples by using a simple lysis method and polymerase chain reaction. J Clin Microbiol. Apr. 1993. (Year: 1993).*

Huang W, Wang J, Bhattacharyya D, Bachas LG. Improving the activity of immobilized subtilisin by site-specific attachment to surfaces. Anal Chem. Nov. 15, 1997 (Year: 1997).*

J. Richens et al., Improving the Accuracy of Medical Diagnosis With Causal Machine Learning, Nature Communications, 9 Pages, (2020).

J. Zhao et al., Antibody Responses to SARS-CovV-2 in Patients of Novel Coronavirus Disease 2019, Oxford University Press For the Infectious Diseases Society of America, 22 Pages, (2020).

Recommendations for National SARS-CoV-2 Testing Strategies and Diagnostic Capacities, World Health Organization, 16 Pages, (Jun. 25, 2021).

D. Yang et al., Diagnostic Excellence, American Medical Association, vol. 326 No. 19, 2 Pages, (Nov. 16, 2021).

A. Maitra et al., Diagnosis and the Illness Experience Ways of Knowing, American Medical Association, 2 Pages, (Oct. 28, 2021).

J. Nascimento Jr. et al., Trends in MERS-CoV, SARS-CoV, and SARS-CoV-2 (Covid-19) Diagnosis Strategies: A Patent Review, Frontiers in Public Health, 15 Pages, (Oct. 27, 2020).

J. Park, Lateral Flow Immunoassay Reader Technologies for Quantitative Point-of-Care Testing, Sensors, 21 Pages, (2022).

Y. Zhang et al., Recent Progress on Rapid Lateral Flow Assay-Based Early Diagnosis of Covid-19, Frontiers in Bioengineering and Biotechnology, 17 Pages, (May 3, 2022).

R. Wolfel et al., Virological Assessment of Hospitalized Patients with COVID-2019, 12 Pages, (Apr. 1, 2020).

N. Okba et al., Severe Acute Respiratory Syndrome Coronavirus 2-Specific Antibody Response in Coronavirus Disease Patients, Emerging Infectious Diseases, 11 Pages, (Jul. 2020).

B. Lou et al., Serology Characteristics of SARS-CoV-2 Infection After Exposure and Post-Symptom Onset, Eur Respir J 2020, 10 Pages, (2020).

N. Guzman et al., Improving Diagnostic Testing and Disease Analysis With IACE, Research Features, 10 Pages, (May 13, 2022).

Y. Deng et al., Recent Advances in Sensitivity Enhancement for Lateral Flow Assay, Microchimica Acta—Springer, 15 Pages, (Oct. 13, 2021).

V. Panferov et al., Electrophoresis-Assisted Multilayer Assembly of Nanoparticles For Sensitive Lateral Flow Immunoassay, 50 Pages.

W. Hsiao et al., Recent Advances in Novel Lateral Flow Technologies For Detection of COVID-19, Biosensors—MDPI, 26 Pages, (Aug. 25, 2021).

Senzo, Senzo's Revolutionary Amplified Lateral Flow (ALF) Platform Delivers Rapid COVID-19 Test Exactly Matching PCR Results in $3^{rd}$-Party Study by the University of Sheffield, 2 Pages, (May 31, 2022).

P. Preechakasedkit et al., Improvement in Sensitivity For Lateral Flow Immunoassay Of Ferritin Using Novel Device Design Based on Gold Enhances Gold Nanoparticles, Scientific Reports, 11 Pages, (2022).

R. Alhabbab et al., Amplifying Lateral Flow Assay Signals for Rapid Detection of COVID-19 Specific Antibodies, Global Challenges, 10 Pages, (2022).

M. Lu et al., Dual-Mode SERS-based Lateral Flow Assay Strips For Simultaneous Diagnosis of SARS-CoV-2 and Influenza a Virus, Nano Convergence, 12 Pages, (2022).

Understanding COVID-19 Antigen Tests, National Collaborating Centre For Infections Diseases, 4 Pages.

B. Boson et al., The SARS-CoV-2 Envelopes and Membrane Proteins Modulate Maturation and Retention of the Spike Protein Allowing Assemble of Virus-Like Particles, JBC Research Article, 13 Pages, (Nov. 23, 2020).

K. Koczula et al., Lateral Flow Assays, Portland Press, 10 Pages, (2016).

G. Posthuma-Trumpie et al., Lateral Flow (immune) Assay: Its Strengths Weaknesses Opportunities and Threats. A literature Survey, Open Access, 14 Pages, (Aug. 13, 2008).

M. Sajid et al., Designs Formats and Applications of Lateral Flow Assay: A literature Review, King Saud University, Journal of Saudi Chemical Society, 17 Pages, (Sep. 16, 2014).

A. Mirica et al., Latest Trends in Lateral Flow Immunoassay (LFIA) Detection Labels and Conjugation Process, Frontiers, Frontiers in Bioengineering and Biotechnology, 22 Pages, (Jun. 14, 2022).

I-Health COVID-19 Antigen Rapid Test, Healthcare Provider Instructions for Use, 22 Pages, (2023).

Y. Yang et al., Evaluating The Accuracy of Different Respiratory Specimens in the Laboratory Diagnosis and Monitoring the Viral Shedding of 2019-nCoV Infections, medRxiv, 17 Pages, (Feb. 17, 2020).

Y. Yang et al., Laboratory Diagnosis and Monitoring the Viral Shedding of SARS-CoV-2 Infection, CellPress Partner Journal, The Innovation, 7 Pages, (Nov. 25, 2020).

Antigen and Molecular Tests for COVID-19, COVID-19 Testing Toolkit, 3 Pages, (2022).

Genetic Variants of SARS-CoV-2 May Lead to False Negative Results with Molecular Tests for Detection of SARS-CoV-2 Letter to Clinical Laboratory Staff and Health Care Providers, U.S. Food & Drug Administration, Letters to Health Care Providers, 1 Pages, (Jan. 8, 2021).

Clinical Spectrum of SARS-CoV-2 Infection, National Institutes of Health, COVID-19 Treatment Guidelines, 1 Page, (Mar. 6, 2023).

D. Oran et al., Prevalence of Asymptomatic SARS-CoV-2 Infection, Annals of Internal Medicine, 7 pages, (Jun. 3, 2020).

D. Buitrago-Garcia et al., Occurrence and Transmission Potential of Asymptomatic and Presymptomatic SARS-CoV-2 Infections: Update of a Living Systematic Review and Meta-Analysis, Plos Medicine, 30 Pages, (May 26, 2022).

C. Chen et al., SARS-CoV-2 Positive Sputum and Feces After Conversion of Pharyngeal Samples in Patients with COVID-19, American College of Physicians, Annals of Internal Medicine, 3 Pages, (2020).

(56) References Cited

OTHER PUBLICATIONS

Y. Zhou et al., Point-of-care COVID-19 Diagnostics Powered by Lateral Flow Assay, Elsevier, Trends in Analytical Chemistry, 15 Pages, (Oct. 2, 2021).
J. Ninnemann et al., Induction of Cross-Reactive Antibody Responses Against the RBD Domain of the Spike Protein of SARS_CoV-2 by Commensal Microbiota, bioRxiv Preprint, 27 Pages, (Oct. 15, 2021).
S. Klompus et al., Cross Reactive Antibodies Against Human Coronaviruses and the Animal Coronavirus Suggest Diagnostics for Future Zoonotic Spillovers, Science Immunology, 17 Pages, (2021).
S. Gunti et al., Polyreactive Antibodies: Function and Quantification, The Journal of Infectious Diseases, Oxford University Press, 5 Paes, (2015).
N. Guzman et al., Immunoaffinity Capillary Electrophoresis in the Era of Proteoforms, Liquid Biopsy and Preventive Medicine: A Potential Impact in the Diagnosis and Monitoring of Disease Progression, Biomolecules, MDPI, 32 Pages, (2021).
J. Li et al., Wireless Lateral Flow Device for Biosensing, Journal of the American Chemical Society, 7 Pages, (2022).
Z. Zhou et al., Properties and Function of Polyreactive Antibodies and Polyreactive Antigen-Binding B Cells, National Institutes of Health, 17 Pages, (Dec. 2007).
J. Fahy et al., Airway Mucus Function and Dysfunction, The New England Journal of Medicine, 15 Pages, (Dec. 2, 2010).
W. Lu et al., The Function of Mucins in the COPD Airway, Springer Science and Business Media, 12 Pages, (May 8, 2013).
M. McKelvey et al., Proteases Mucus and Mucosal Immunity in Chronic Lung Disease, International Journal of Molecular Sciences, MDPI, 21 Pages, (May 9, 2021).
L. Kaler et al., Influenza A Virus Diffusion Through Mucus Gel Networks, Communications Biology, 9 Pages, (2022).
J. Leal et al., Physicochemical Properties of Mucus and Their Impact on Transmucosal Drug Delivery, HHS Public Access, 46 Pages, (Oct. 30, 2017).
N. Reznik et al., Intestinal Mucin is a Chaperone of Multivalent Copper, Cell Press, Elsevier Inc., 22 Pages, (Oct. 27, 2022).
J. Voynow et al., Mucins Mucus and Sputum, Chest Journal, 8 Pages, (Feb. 2009).
B. Nicholas et al., Shotgun Proteomic Analysis of Human-Induced Sputum, Proteomics Journal, 12 Pages, (May 5, 2006).
D. Pacheco et al., Disassembling the Complexity of Mucus Barriers to Develop a Fast Screening Tool for Early Drug Discovery, Journal of Materials Chemistry B, 13 Pages, (2019), Royal Society of Chemistry.
J. Schofield et al., Large-Scale Label-Free Quantitative Mapping of the Sputum Proteome, Journal of Proteome Research, 31 Pages, (May 8, 2018).
S. Gharib et al., Induced Sputum Proteome in Health and Asthma, National Institutes of Health, 21 Pages, (Dec. 2011).
Z. Zhang et al., Proteomic Profiling Reveals a Distinctive Molecular Signature for Critically Ill COVID-19 Patients Compare with Asthma and Chronic Obstructive Pulmonary Disease, International Journal of Infectious Diseases, 10 Pages, (Jan. 2, 2022).
Z. Zhang et al., The Proteomic Characteristics of Airway Mucus From Critical Ill COVID-19 Patients, Life Sciences, 11 Pages, (Jan. 14, 2021).
D. Harper et al., Bacteriophages and Biofilms, Open Access Antibiotics, 15 Pages, (Jun. 25, 2014).
A. Sousa et al., Pseudomonas Aeruginosa Diversification During Infection Development in Cystic Fibrosis Lungs—A Review, Open Access Pathogens, 24 Pages, (Aug. 18, 2014).
R. Mishra et al., Natural Anti-Biofilm Agents: Strategies to Control Biofilm-Forming Pathogens, Frontiers in Microbiology, 23 Pages, (Oct. 29, 2020).
P. Sanchez-Vizuete et al., Pathogens Protection Against the Action of Disinfectants in Multispecies Biofilms, Frontiers in Microbiology, 12 Pages, (Jul. 14, 2015).
R. Von Browski et al., Biofilms and Coronavirus Reservoirs: a Perspective Review, American Society for Microbiology, Applied and Environmental Microbiology, vol. 87 Issue 18, 14 Pages, (Sep. 2021).
E. Poukka et al., Detection of SARS-CoV-2 Infection in Gargle Spit and Sputum Specimens, American Society for Microbiology, Microbiology Spectrum, vol. 9 Issue 1, 8 Pages, (Aug. 25, 2021).
R. Terracciano et al., Peptidome Profiling of Induced Sputum by Mesoporous Silica Beads and MALDI-TOF MS for Non-Invasive Biomarker Discovery of Chronic Inflammatory Lung Diseases, Proteomics Journal, 13 Pages, (May 30, 2011).
Y. He et al., Value of Viral Nucleic Acid in Sputum and Feces and Specific IgM/IgG in Serum for the Diagnosis of Coronavirus Disease 2019, Frontiers in Cellular and Infection Microbiology, 6 Pages, (Aug. 6, 2020).
L. Peng et al., SARS-CoV-2 Can be Detected in Urine Blood Anal Swabs and Oropharyngeal Swabs Specimens, Journal of Medical Virology, 5 Pages, (Apr. 22, 2020).
L. Huang et al., Swab and Sputum SaRS-CoV-2 RNA-Negative, CT-Positive, Symptomatic Contacts of COVID-19 Cases: A Hypothesis-Generating Prospective Population-Based Cohort Study of Eight Clusters, Frontiers in Medicine, 14 Pages, (Aug. 17, 2021).
S.D. Aaron et al., Sputum Versus Bronchoscopy for Diagnosis of Pseudomonal Aeruginosa Biofilms in Cystic Fibrosis, European Respiratory Journal, 7 pages, (Jun. 11, 2004).
R. Gray et al., Sputum Proteomics in Inflammatory and Suppurative Respiratory Diseases, American Journal of Respiratory and Critical Care Medicine, vol. 178, 9 pages, (Jun. 17, 2008).
S. Saleem et al., Sputum Testing as the New Mass Screening Method for COVID-19 Patients in India—A Public Health Perspective, International Journal of Preventive Medicine, 3 Pages, (2022).
T. Kadja et al., Low-Cost Real-Time Polymerase Chain Reaction System for Point-of-Care Medical Diagnosis, Sensors, MDPI, 14 Pages, (Mar. 17, 2022).
T. Abe et al., A Patient Infected With SARS-CoV-2 Over 100 Days, QJM: An International Journal of Medicine, vol. 114 No. 1, 3 Pages, (Oct. 16, 2020).
G. Patriquin et al., Generation of False-Positive SARS-CoV-2 Antigen Results with Testing Conditions Outside Manufacturer Recommendations: A Scientific Approach to Pandemic Misinformation, American Society for Microbiology, Microbiology Spectrum, 15 Pages, (Oct. 20, 2021).
Y. Zhou et al., Point-of-Care COVID-19, Diagnostics Powered by Lateral Flow Assay, Trends in Analytical Chemistry, 15 Pages, (Oct. 2, 2021).
F. Shen et al., Sputum Analysis, National Library of Medicine, National Center for Biotechnology Information, 1 page, (Feb. 20, 2023).
A.V. Raveendran et al., Long COVID: An Overview, Diabetes & Metabolic Syndrome: Clinical Research & Reviews, 8 Pages, (Apr. 6, 2021).
R. Rubin, As Their Numbers Grow COVID-19 "Long Haulers" Stump Experts, 5 Pages, (Sep. 23, 2020).
M. Marshall, COVID-19's Lasting Misery, Spring Nature Limited, vol. 585, 3 Pages, (Sep. 17, 2020).
C. Schmidt, COVID-19 Long Haulers, Nature Biotechnology, vol. 39, 6 Pages (Aug. 2021).
A. Sansone et al., The Sexual Long COVID(SLC): Erectile Dysfunction as a Biomarker of Systemic Complications for COVID-19 Long Haulers, Sexual Medicine Reviews, 15 Pages, (2021).
R. Ramakrishnan et al., Unraveling the Mystery Surrounding Post-Acute Sequelae of COVID-19, Frontiers In Immunology, 16 Pages, (Jun. 30, 2021).
Z. Swank et al., Persistent Circulating SARS-CoV-2 Spike is Associated With Post-Acute COVID-19 Sequelae, MedRxiv, 16 Pages, (Jun. 16, 2022).
Y. Chen et al., The Presence of SARS-CoV-2 RNA in the Feces of COVID-19 Patients, Journal of Medical Virology, 8 Pages, (Mar. 31, 2020).
B. Ince et al., Lateral Flow Assays For Viruses Diagnosis: Up-To-Date Technology and Future Prospects, Trends in Analytical Chemistry, 19 Pages, (Jul. 5, 2022).

(56) References Cited

OTHER PUBLICATIONS

O. Filchakova et al., Review of COVID-19 Testing and Diagnostic Methods, Talanta, 32 Pages, (Mar. 31, 2022).
G. Alhamid et al., SARS-CoV-2 Detection Methods: A Comprehensive Review, Saudi Journal of Biological Sciences, 15 Pages, (Sep. 27, 2022).
M. Mostafa et al., Current Trends in COVID-19 Diagnosis and its New Variants in Physiological Fluids: Surface Antigens, Antibodies, Nucleic Acids, and RNA Sequencing, Trends in Analytical Chemistry, 26 Pages, (Aug. 30, 2022).
S. Songca, Applications of Nanozymology in the Detection and Identification of Viral Bacterial and Fungal Pathogens, International Journal of Molecular Sciences, MDPI, 25 Pages, (Apr. 22, 2022).
S. Rink et al., Highly Sensitive Interleukin 6 Detection by Employing Commercially Ready Liposomes in an LFA Format, Springer, 11 Pages, (Nov. 13, 2021).
R. Maher et al., The Relationship Between Lung Disease Severity and the Sputum Proteome in Cystic Fibrosis, Respiratory Medicine, 9 Pages, (Sep. 30, 2022).
A. Bacura et al., Current Status of the Lateral Flow Immunoassay for the Detection of SARS-CoV-2 in Nasopharyngeal Swabs, Biochem Med, 10 Pages, (Apr. 10, 2021).
F. Di Nardo et al., Ten Years of Lateral Flow Immunoassay Technique Applications: Trends Challenges and Future Perspectives, Sensors, MDPI, 33 Pages, (Jul. 30, 2021).
B. Shan et al., Multiplexed Nanomaterial-Based Sensor Array for Detection of COVID-19 in Exhaled Breath, ACS Nano, 8 Pages, (Aug. 18, 2020).
N. Guzman et al., A Two-Dimensional Affinity Capture and Separation Mini-Platform for the Isolation Enrichment and Quantification of Biomarkers and Its Potential Use for Liquid Biopsy, Biomedicines, MDPI, 37 Pages, (Jul. 30, 2020).
H. Xu et al., An Ultraportable and Versatile Point-of-Care DNA Testing Platform, Science Advances Research Article, 10 Pages, (Apr. 22, 2020).
Y. Wang et al., Sputum Characteristics and Airway Clearance Methods in Patients with Severe COVID-19, Medicine, 5 Pages, (Oct. 21, 2020).
A. Urusov et al., Towards Lateral Flow Quantitative Assays: Detection Approaches, Biosensors, MDPI, 16 Pages, (Jul. 17, 2019).
N. Guzman et al., From a Central Laboratory to the Bedside: a Point-of-Care Instrument for Monitoring Wellness and Disease Using Two-Dimensional Immunoaffinity Capillary Electrophoresis Technology, Archives of Biomedical Research, Scientific Open Access Journals, vol. 1 Issue 1, 16 Pages, (2018).
K. Cladwell, The Virome in Host Health and Disease, HHS Public Access, 20 Pages, (May 19, 2016).
A. Branche et al., Detection of Respiratory Viruses in Sputum from Adults by Use of Automated Multiplex PCR, Journal of Clinical Microbiology, vol. 52 No. 10, 7 Pages, (Oct. 2014).
M. Honkinen et al., Viruses and Bacteria in Sputum Samples of Children with Community-Acquired Pneumonia, Clinical Microbiology and Infection, vol. 18 No. 3, (Mar. 2012).
N. Guzman et al., Immunoaffinity Capillary Electrophoresis: A New Versatile Tool For Determining Protein Biomarkers in Inflammatory Processes, Electrophoresis Journal, 64 Pages, (2011).
A. Jones et al., Diagnosis of Respiratory Viral Infections in Cystic Fibrosis by PCR Using Sputum Samples, European Respiratory Journal, vol. 38 No. 6, 2 Pages.
R. Gray et al., Sputum Proteomics in Inflammatory and Suppurative Respiratory Diseases, American Journal of Respiratory and Critical Care Medicine, vol. 178, 9 Pages, (Jun. 19, 2008).
T.H. Harju et al., Pathogenic Bacteria and Viruses in Induced Sputum or Pharyngeal Secretions of Adults with Stable Asthma, Thorax, 6 Pages, (Mar. 3, 2006).

\* cited by examiner

METHOD AND SYSTEM FOR EXPOSING HIDDEN OR MASKED ANTIGENIC SITES OF VIRAL SPECIMENS PRESENT IN BIOSAMPLES USING A HOME-BASED COVID-19 RAPID LATERAL FLOW IMMUNOASSAY TEST

BACKGROUND OF THE INVENTION

Field of the Invention

The field of the invention relates generally to the analysis of chemical and biological materials and, more particularly, to a method and system for detection of disease including analysis of antigenic reactive components of viral specimens obtained from biosamples against conjugated anti-SARS-COV-2 antibodies.

Description of the Related Art

Diagnosis is a fundamental part of clinical medicine and is a prerequisite for the delivery of high-quality, effective care [Yang et al., *Journal of the American Medical Association* 2021, volume 326, pages 1905-1906); Maitra el al., *Journal of the American Medical Association* 2021, volume 326, pages 1907-1908]. Providing accurate and accessible diagnoses is a fundamental challenge for global healthcare systems [Richens et al., *Nature Communications* 2020, 11, 3923, doi: 10.1038/s41467-020-17419-7].

Timely and accurate diagnostic testing plays an important role in preventing and controlling the spread of COVID-19 and any other infectious disease and is the cornerstone of the efforts to provide appropriate treatment for patients, to limit further spread of the virus and ultimately to eliminate the virus from human society [Zhao el al., Clinical Infectious Diseases 2020, volume 71, issue 16, pages 2027-2034; doi: 10.1093/cid/ciaa344]. Several diagnostic techniques for SARS-COV-2 by the World Health Organization have been recommended for national SARS-COV-2 testing strategies and diagnostic capacities, because diagnostic testing for SARS-COV-2 is a critical component to the overall prevention and control strategy for COVID-19. According to these recommendations, at least three different diagnostic techniques for SARS-CoV-2 are available: (1) detection of viral RNA, through manual or nucleic acid amplification tests (NAAT), such as real time reverse-transcription polymerase chain reaction (rRT-PCR); (2) detection of viral antigens through immunodiagnostic techniques, such as lateral flow assays (LFAs), commonly called rapid diagnostic tests or Ag-RDTs; and (3) detection of host antibodies through serological techniques, such as LFAs, enzyme linked immunosorbent assays (ELISAs), and chemiluminescence immunoassays (CLIAs). In general, there is a wide range of conventional tests available with different detection methodologies, levels of specificity and sensitivity, detection time, and with an extensive range of prices [Nascimento Junior et al., *Frontiers in Public Health* 2020, volume 8, 563095; doi: 10.3389/fpubh.2020.563095; Park, Sensors (Basel) 2022, volume 22, issue 19, 7398; doi: 10.3390/s22197398; Zhang et al., *Frontiers in Bioengineering and Biotechnology* 2022, 10:866368; doi: 10.3389/fbioe.2022.866368].

NAAT is the most sensitive and specific assay and is therefore recommended as the reference standard. Ag-RDTs offer an opportunity to increase the availability and speed of testing in appropriate scenarios. Antibody detection is usually not recommended for diagnosis of COVID-19, as it may take up to two weeks for the host antibodies to be produced, but it plays an important role in the detection of past infections for research and surveillance [Zhao el al., Clinical Infectious Diseases 2020, volume 71, issue 16, pages 2027-2034; doi: 10.1093/cid/ciaa344; Wölfel et al., *Nature* 2020, volume 581, pages 465-469; doi: 10.1038/s41586-020-2196-x; Okba et al., *Emerging* Infectious Diseases, volume 26, issue 7, pages 1478-1488; doi: 10.3201/eid2607.200841; Lou et al., *Journal of Respiratory Diseases* 2020, 56:2000763; doi: 10.1183/13993003.00763-2020]. Other techniques, such as the two-dimensional capture-separation immunoaffinity capillary electrophoresis (IACE) can provide more detailed information, such as proteoforms, for the simultaneous determination of multiple biomarkers during the development of a communicable disease [Guzman, U.S. Pat. No. 11,287,386, granted on Mar. 29, 2022; Guzman et al., *Research Features* May 13, 2022; doi: 10.26904/RF-141-2652756006]. Attempts to enhance signal amplification and sensitivity using lateral flow immunoassay (LFIA) tests have been reported for viral detection and inflammatory biomarkers [Deng et al., *Mikrochim Acta* 2021, volume 188, issue 11, 379; doi:10.1007/s00604-021-05037-z; Panterov et al., *Angewandte Chemie* International Edition in English 2022, e202215548; doi: 10.1002/anie.202215548; Mehra et al., U.S. Pat. No. 11,255,854, Feb. 22, 2022; Cary., U.S. Pat. No. 10,458,978, Oct. 29, 2019; Hsiao et al., *Biosensor* 2021, volume 11, issue 9, 295; doi:10.3390/bios11090295; Zhang et al., *Frontiers in Bioengineering and Biotechnology* 2022, 10:866368, doi: 10.3389/fbioe.2022.866368; Li et al., *Journal of the American Chemical Society* 2022; volume 144, issue 34, pages 15786-15792; doi: 10.1021/jacs.2c06579; Preechakasedkit et al., *Scientific Reports* 2022, volume 12, 7831; doi: 10.1038/s41598-022-11732-5; Alhabbah et al., *Global Challenges* 2022, volume 6, 2200008; doi:10.1002/gch2.202200008; Lu et al., *Nano Convergence* 2022, volume 9, 39; doi: 10.1186/s40580-022-00330-w]. LFIA test systems are fully consistent with the world's modern concept of 'point-of-care testing', finding a wide range of applications not only in human medicine, but also in ecology, veterinary medicine, and agriculture [Andryukov, *AIMS Microbiology* 2020, volume 60, issue 3, pages 280-304; doi: 10.3934/microbiol.2020018].

Rapid diagnostic tests (Ag-RDTs), using primarily lateral flow assays, which are also known as immunochromatographic assays or simply strip tests, play a crucial role in curbing COVID-19 infections. They are designed to detect a portion of protein, known as antigen, of SARS-COV-2 in biosamples, primarily nasal and nasopharyngeal samples obtained with a swab as indicated by commercial kits that have been authorized for non-prescription home use by the U.S. Food and Drug Administration (FDA) under an Emergency Use Authorization (EUA). These products have been authorized only for the detection of antigenic proteins present in SARS-COV-2, such as nucleocapsid protein antigen, and not for any other viruses or pathogens. Typically, a COVID-19 antigen home test package contains a test cassette, platform, or a card, where the flow lateral immunochromatography test is going to be performed, a sample collection tube containing an extraction buffer with some detergent, for example a solution carrying Triton X-100, Tween-20, or Nonidet P-40, a disposable nasal swab, and a tube holder. The sample is collected using the swab, as directed by the instructions provided by the manufacturer of the test, followed by a squeezing-mixing protocol of the sample-containing swab in the extraction buffer tube carrying the detergent liquid extraction. The purpose of the detergent is to partially fragment and break apart the coat or envelope surrounding the virus and disrupt the virus to expose the antigenic portions of the virus. The SARS-COV-2 virus has several antigens, including its nucleocapsid protein, phosphoprotein, and spike proteins. Consistently, the nucleocapsid protein is also one of the most abundant proteins of the SARS-COV-2 virus. The four structural proteins of the SARS-CoV-2 virus are: spike (S), envelope (E), membrane (M), and nucleoprotein (N) proteins [Boson et al., *Journal of Biological Chemistry* 2021, volume 296, 100111; doi:10.1074/jbc.RA120.016175; Zhang et al., *Frontiers in Bioengineering and Biotechnology* 2022, 10:866368; doi: 10.3389/fbioe.2022.866368].

Once the sample is collected and soaked in the detergent-containing extraction buffer or solution, a few drops of the disrupted sample with its constituent components is loaded onto the inlet part of the test platform, or sample well, where the migration of the sample will occur through the strip. The principle behind the lateral flow assay is simple, a liquid sample, or its extract, containing the analyte of interest moves laterally upward without the assistance of external forces, just by capillary action, through various zones of a paper or polymeric made strip to which molecules, mainly an antibody, that can interact and bind to the analyte are attached [Koczula et al., *Essays in Biochemistry* 2016, volume 60, issue 1, pages 111-120; doi: 10.1042/EBC20150012; Posthuma-Trumie et al., *Analytical and Bioanalytical Chemistry* 2009, volume 393, pages 569-582; doi:10.1007/s00216-008-2287-2; Sajid et al., *Journal of Saudi Chemical Society* 2015, volume 19, pages 689-705; doi:10.1016/j.jscs.2014.09.001; Andryukov, *AIMS Microbiology* 2020, volume 60, issue 3, pages 280-304; doi: 10.3934/microbiol.2020018]. The migrating antigenic viral proteins interact with SARS-COV-2-antigen-specific antibodies that have been conjugated with color indicators, usually gold nanoparticles. If the SARS-COV-2 antigens are present in the sample, they will be captured by the antigen-specific immobilized antibodies and then seen as colored lines on the strip test, referred to as a T line, corresponding to the test line, and indicating a positive test for COVID-19. The color of gold nanospheres in suspension varies from wine red to dark shades of color in case aggregation occurs [Mirica et al., *Frontiers in Bioengineering and Biotechnology* 2022; vol. 10, 922772; doi: 10.3389/fbioe.2022.922772]. A colored line also appears on the test strip corresponding to the control line, referred to as a C line, using a different type of antibody, and following the protocol for the best performance of the test as indicated by the test manufacturers as shown in FIG. 1.

Conventional rapid antigen tests are convenient because they are easy to use and provide results quickly, typically within 15 or 20 minutes, high-throughput, and less workload. Another benefit is that antigen tests can be relatively inexpensive, around US $8.00-$10.00 per test. In contrast, conventional PCR tests usually require laboratory equipment and specialized technicians, take 12 hours to several days to get the results and cost around US $100.00 or more, if a person is not waived for payment of the PCR test. A major drawback of these rapid antigen tests is the interpretation of the results. The antigen is generally detectable in anterior nasal swab specimens during the acute phase of infection. If one gets a negative result but still feels sick, it is possible that one has obtained a false negative test. Negative results are presumptive and confirmation with a molecular assay, if necessary for patient management, may be performed. Negative results do not rule out COVID-19 and should not be used as the sole basis for treatment or patient management decisions, including infection control decisions. Positive results indicate the presence of viral antigens, but clinical correlation with past medical history and other diagnostic information is necessary to determine infection status. Positive results do not rule out bacterial infection or co-infection with other viruses. For example, the iHealth COVID-19 Antigen Rapid Test does not differentiate between SARS-COV and SARS-COV-2 viruses. The agent detected may not be the definite cause of a microbial disease. Rapid COVID-19 antigen home test products have been authorized only for the detection in anterior nasal swab specimens of antigenic proteins present in SARS-COV-2, such as nucleocapsid protein antigen, and not for any other viruses or pathogens.

Regarding the accuracy of conventional tests, the source of the sample seems to be very important. According to the results of Yang et al. [Yang et al., medRxiv preprint doi: 10.1101/2020.02.11.20021493; Yang et al., *The Innovation* 2020, 1:100061; doi:10.1016/j.xinn.2020.100061], samples obtained by bronchoalveolar lavage fluid (BALF) possessed 100% of positive rate, followed by sputum samples, nasopharyngeal swabs, and then oropharyngeal swabs, when the tests were performed by molecular diagnosis using the quantitative reverse transcription polymerase chain reaction (qRT-PCR) detecting SARS-COV-2 RNA. Yang et al. concluded that sputum is most sensitive for routine laboratory diagnosis of COVID-19, followed by nasal swabs. The collection of BALF specimens has the disadvantage of requiring both a suction device and a skilled operator; also, it is painful for the patient. Therefore, BALF samples are not feasible for the routine diagnosis and monitoring of the SARS-COV-2 coronavirus. Instead, collection of a nasal swab, and sputum is rapid, simple, and safe. Throat swabs were not recommended for viruses' detection, which resulted in a large proportion of false negative results. Additionally, the virus can also be detected in feces, urine, or blood.

Yang et al. [Yang et al., medRxiv preprint doi: 10.1101/2020.02.11.20021493; Yang et al; *The Innovation* 2020, 1:100061; doi: 10.1016/j.xinn.2020.100061], also raised some questions about some limitations of their studies, assuming that the qRT-PCR assay is 100% accurate, which cannot be guaranteed and may contribute to false-positive or false-negative results. The U.S. Food and Drug Administration (FDA) has alerted clinical laboratory staff and health care providers that false negative results may occur with any molecular test for the detection of SARS-COV-2 if a mutation occurs in part of the virus' genome assessed by that test. The recently identified B.1.1.7 variant carries many mutations, including a double deletion at positions 69 and 70 on the spike protein gene (S-gene), which is the mutation that appears to impact the pattern of detection when using the TaqPath COVID-19 Combo Kit and the Linea COVID-19 Assay Kit. Therefore, early identification of this variant in patients may help reduce further spread of infection of the B.1.1.7 variant, which has been identified with an increased risk of transmission.

Timely and accurate testing is an essential tool in preventing and controlling the spread of SARS-COV-2 and when implemented strategically provides cost-effective implementation of clearly defined public health countermeasures. There are five cases of COVID-19 patients, including patients with asymptomatic or pre-symptomatic infection, patients suffering of mild illness, moderate illness, severe illness, and those patients suffering of critical illness. Patients with certain underlying comorbidities are at higher risk of progressing to severe COVID-19. It has been suspected that infected persons who remain asymptomatic play a significant role in the ongoing pandemic, but their relative number and effect have been uncertain. Because of the high risk for silent spread by asymptomatic persons, it is imperative that testing programs include those without symptoms [Oran et al., *Annals of Internal Medicine* 2020, doi: 10.7326/M20-3012; Buitrago-Garcia et al., *PLOS Medicine* 2022, volume 19, issue 5: e1003987; doi: 10.1371/journal.pmed.1003987; Chen et al., 2020, *Annals of Internal Medicine*; doi: 10.7326/M20-0991]. The diagnosis of SARS-COV-2 infection remains the main driving force to alleviate the COVID-19 pandemic. Various rapid diagnostic technologies using portable LFIA platform are known, some of which have been developed into test kits for rapidly diagnosing COVID-19. However, several challenges remain to be addressed to improve the performance of LFIA tests in controlling the COVID-19 epidemic [Zhou et al., *Trends in Analytical Chemistry* 2021, volume 145, 116452; doi: 10.1016/j.trac.2021.116452].

The accurate and consistent detection of antigens of interest in complex samples such as biological fluids remain a challenge. It is estimated that the human microbiota contains several millions of genes, thus potentially providing a plethora of epitopes for antibodies. Such epitopes may resemble host proteins, potentially inducing autoimmunity, while others may resemble proteins from other microorganisms and mediate cross-reactivity as described in [Ninnemann et al., bioRxiv preprint doi:10.1101/2021.08.08.455272]. Ninnemann et al. demonstrated that microbiota can be recognized by the antibodies raised against the receptor-binding domain (RBD) of the SARS-COV-2 spike protein. Similarly, it has been suggested that the accuracy of serological tests can be perturbed by antibody cross-reactivity with similar antigens of the animal coronavirome, and the multiple CoV strains that infect humans (hCoVs) [Klompus et al., *Science Immunology* 2021, 6, eabe9950]. It has been recognized that although increasing amounts of data are accumulating on antibody cross-reactivity between hCoVs, cross-reactivity with the animal coronavirome and its diagnostic potential for detecting future spillovers of a CoVs to humans in incompletely understood [Klompus et al., *Science Immunology* 2021, 6, eabe9950]. The existence of polyreactive antibodies showing different binding patterns and affinities when evaluated with a large panel of antigens have been discussed previously [Gunti et al., *The Journal of Infectious Diseases*, volume 212, issue suppl. 1, pages S42-S46; doi: 10.1093/infdis/jiu512; Guzman et al., Research Features May 13, 2022; doi: 10.26904/RF-141-2652756006; Guzman et al., *Biomolecules,* 11(10), 1443, 2021; Zhou et al., *Journal of Autoimmunity* 2007, volume 29, issue 4, pages 219-228].

It has been described that mucus is a hydrogel (e.g., meshwork) composed of about 95-97% of water, 3% of solids, including 1% salts and containing large polymeric mucin glycoproteins, globular proteins, and lipid surfactants [Fahy et al., *New England Journal of Medicine* 2010, volume 363, issue 23, pages 2233-2247; Lu et al., *Current Respiratory Care Reports* 2013, volume 2, pages 155-166]. However, in chronic lung disease the solid content can increase to up to 15% as a result of airway dehydration coupled with increased mucin expression and hypersecretion. These layers of the mucus meshwork are capable of trapping cell debris and pathogens [Mckelvey et al., *International Journal of Molecular Sciences* 2021, volume 22, 5018; doi: 10.3390/ijms22095018]. In order to prevent infection, mucus in the lung must effectively trap inhaled pathogens and the mechanism by which this is achieved are important to understanding of innate host defenses [Kaler et al., *Communications Biology* 2022, 5, 249; doi: 10.1038/s2003-022-03204-3]. Mucus is continuously produced, secreted, and finally digested, recycled, or discarded, and its main functions include lubrication of the epithelia, maintenance of a hydrated layer, exchange of gases and nutrients with the underlying epithelium, as well as a barrier to pathogens and foreign substances [Leal et al., *International Journal of Pharmacy* 2017, volume 532, issue 1, pages 55-572; doi:10.1016/j.ijpharm.2017.09.018]. Mucin glycoproteins may also facilitate the removal of contaminants and waste product from the body [Reznik et al., *Cell* 2022, volume 185, pages 4206-4215; doi: 10.1016/j.cell.2022.09.021]. The numerous activities of mucins are enabled by the large sizes, dynamic conformations, post-translational modifications, and extensive intermolecular interactions of mucins. However, the same features that contribute to mucin functionality also complicate the study of these glycoproteins. Consequently, many questions remain regarding the mechanisms of mucin assembly, their physical and chemical capabilities, and their physiological contributions to the critical interfaces between animals and their environments [Reznik et al., *Cell* 2022, volume 185, pages 4206-4215; doi: 10.1016/j.cell.2022.09.021].

Sputum is a thick complex mucus. Mucus strands form cross links, producing a sticky, elastic gel. The expectorated mucus is called sputum, which about 95% water, 3% proteins, including mucin glycoproteins and other glycated proteins, and 1% salts and other substances such as lipid surfactants [Voynow et al., *Chest* 2009, volume 135, issue 2, pages 505-512; doi: 10.1378/chest.08-0412]. Goblet cells of the mucous membranes and the submucosal glands of the respiratory systems, gastrointestinal, and reproductive system are responsible for the secretion of mucus. The secreted mucins are long fibrous peptides coated with a complex array of glycans. The respiratory mucins of a single person probable contain several hundred different glycans, and there are considerable variations between individuals [Cone, Mucosal Immunology (Third Edition) 2005, Chapter 4—*Mucus*; doi: 10.1016/B978-012491543-5/50008-5]. Disassembling the complexity of mucus barriers still represent an unmet challenge [Pacheco et al., *Journal of Materials Chemistry B* 2019, volume 7, issue 32, pages 4940-4952]. Many pathogens can be sequestered or encased within the sputum by another layer of protection named biofilms. Studies on the origins of proteins in sputum have demonstrated that they are numerous and complex, revealing distinctive molecular signatures [Nicholas et al., *Proteomics* 2006, volume 6, pages 4390-4401; doi:10.1002/pmic.200600011; Burg et al., *Journal of Proteome Research* 2018, volume 17, issue 6, pages 2072-2091/acs.jproteome.8b00018; Gharib et al., *Journal of Allergy and Clinical Immunology* 2011, volume 128, issue 6, pages 1176-1184e; doi: 10.1016/j.jaci.2011.07.053; Terracciano et al., *Proteomics* 2011, volume 11, issue 16, pages 3402-3414; doi:10.1002/pmic.201000828; Zhang et al., *International Journal of Infectious Diseases* 2022, volume 116, pages 258-267; doi:10.1016/j.ijid.2022.01.008; Zhang et al., *Life Sciences* 2011, volume 269, 119046; doi:10.1016/j.lfs.2021.119046].

In general, biofilms are aggregation of cells, which may be eukaryotic or prokaryotic in nature, surrounded by a self-produced matrix composed of extracellular polymeric substances (EPS) produced, at least in part, by cells within the biofilm. This EPS consists primarily of long chain sugars or exopolysaccharides, DNA, proteins, lipids, and other macromolecules, the precise nature of which can be highly variable [Harper et al., *Antibiotics* 2014, volume 3, pages 270-284; doi:10.3390/antibiotics3030270]. Biofilms are recognized as an important issue in human disease management due to their notorious resistance, achieving 10- to 1000-fold higher tolerance to antimicrobial agents than corresponding planktonic bacteria. Biofilm resistance has multifactorial nature resulting from the combination of several mechanisms, including restricted penetration of antimicrobials through the exopolysaccharide-protein matrix, slow growth of microorganisms within biofilms caused by nutrient and oxygen restriction, and accumulated metabolic wastes, and quorum-sensing molecules [Sousa et al., *Pathogens* 2014, volume 3, issue 3, pages 680-703; doi:10.3390/pathogens3030680; Mishra et al., *Frontiers in Microbiology* 2020, 11, 566325; doi:10.3389/fmicb.2020.566325]. Biofilms are mucilaginous communities of microorganisms such as bacteria, archaea, fungi, molds, algae, viruses, or protozoa, or mixtures thereof that grow on various surfaces [Mordas et al., U.S. Pat. No. 9,591,852 B2, Mar. 14, 2017]. Biofilms are also found in man-made environments, where they may be related to nosocomial infections, food spoilage, and damage to industrial pipelines or equipment [Sanchez-Vizuete et al., *Frontiers in Microbiology* 2015, 6, 705; doi: 10.3389/fmich.2015.00705]. It has been established that the majority of microorganisms on earth live in biofilms which are surface-attached or floating, with the evolutionary purpose of protection nutrition or strengthening survival [Von Borowski et al., *Applied and Environmental Microbiology* 2021, volume 87, issue 18, e00859-21; doi:10.1128/AEM.00859-21].

There is evidence that SARS-COV-2 can be found in throat swab, gargle, spit, sputum, blood, urine, and feces specimens when testing for the presence of viral RNA by the golden standard real time reverse-transcription polymerase chain reaction (rRT-PCR) assay, and/or by quantitative real-time polymerase chain reaction (qRT-PCR) assay, for diagnosing COVID-19 [Poukka et al., *Microbiology Spectrum* 2021, 9(1), e000; doi:10.1128/Spectrum.00035-21; He et al., *Frontiers in Cellular and Infection Microbiology* 2020, 10, 445; doi:10.3389/fcimb.2020.00455; Peng et al., *Journal of Medical Virology* 2020, volume 92, pages 1676-1680; doi: 10.1002/jmv.25936]. This test alone might be insufficient. It has been confirmed that some COVID-19 cases become symptomatic and radiographically positive, but they remain testing negative for SARS-COV-2 RNA throughout the disease course when all testing agents work normally. In China, the inclusion of clinically diagnosed cases with characteristic radiological findings, regardless of the RNA testing result, greatly contributed to control of COVID-19 in Wuhan [Huang et al., *Frontiers in Medicine* 2021, 8, 685544; doi: 10.3389/fmed.2021.685544].

SARS-COV-2 has multiple shedding ways and a more prolonged survival time in sputum. A comprehensive understanding of the viral shedding period in human body is extremely helpful to determine the time of release of a patient from quarantine or discharge from the hospital [He et al., *Frontiers in Cellular and Infection Microbiology* 2020, 10, 445; doi: 10.3389/fcimb.2020.00455]. It has been hypothesized that SARS-COV-2 may be found occult, in the form of a biofilm, harbored in the airway lacuna with other pathogenic microorganisms, which may be the cause of pulmonary cavities in certain patients with COVID-19 [He et al., *Frontiers in Cellular and Microbiology Infection* 2022, 12, 971933; doi:10.3389/fcimb.2022.971933]. Biofilms may play a role in pathogenicity modulation of coronaviruses, in their ability to persist in reservoir hosts, in the environment, and their transmissibility [Von Borowski et al., *Applied and Environmental Microbiology* 2021, volume 87, issue 18, e00859-21; doi: 10.1128/AEM.00859-21].

Sputum, described as a non-invasive procedure for collection, provides as much information as bronchoscopy, a semi-invasive procedure performed under sedation and may need in certain cases general anesthesia, for the study of chronic *Pseudomona aeruginosa* infection in patients with stable cystic fibrosis [Aaron et al., *European Respiratory Journal* 2004, volume 24, pages 631-637; doi: 10.1183/09031936.04.00049104]. Induced sputum is a conventional technique that is commonly utilized for sampling airway and cells and shown to provide diagnostic and mechanistic insights into a number of lung diseases including asthma, COPD, sarcoidosis, and cystic fibrosis. Induced sputum is comprised of a cellular part and a fluid phase, each of which represent constituents from various sources including airway epithelial cells, inflammatory cells, airway secretions, and even bacterial/viral components [Gharib et al., 2011, *Journal of Allergy and Clinical Immunology* 2011, volume 128, issue 6, pages 1176-1184.e6; doi:10.1016/j.jaci.2011.07.053; Gray et al., *American Journal of Respiratory and Critical Care Medicine* 2008, volume 178, issue 5, pages 444-452; doi: 10.1164/rccm.200703-4090C]. Induced sputum is increasingly recognized as a suitable alternative to bronchoalveolar lavage, bronchial washing, and nasal lavage fluid [Nicholas et al., *Proteomics* 2006, volume 6, issue 15, pages 4390-4401; doi:10.1002/pmic.200600011]. Sputum testing is beginning to be considered as a mass screening method for COVID-19 patients in India [Saleem et al., *International Journal of Preventive Medicine* 2022, volume 13, 86; doi: 10.4103/ijpvm.IJPVM_323_20]. Chen et al. [*Annals of Internal Medicine* 2020; doi: 10.7326/M20-0991] reported that testing sputum and fecal samples, after conversion of their pharyngeal samples from positive to negative, using real-time quantitative fluorescence polymerase chain reaction (RT-qPCR) for SARS-Cov-2 RNA, they remained positive for 13 days when testing feces, and remained positive for 39 days when testing sputum. To perform RT-qPCR requires expensive instruments, trained personnel to perform the assay, and an appropriate laboratory facility [Kadja et al., Sensors (Basel) 2022, volume 22, issue 6, 2320; doi: 10.3390/s22062320]. Experiments performed by Chen et al. [Chen et al., *Annals of Internal Medicine* 2020, doi: 10.7326/M20-0991], demonstrated that assaying with the real-time quantitative fluorescence polymerase chain reaction (RT-qPCR) in sputum samples, it was possible to confirm in 22 patients using 262 sputum samples that the patients resulted positive for SARS-COV-2 virus up to 39 days, after the obtained pharyngeal samples were negative.

Experiments were reported observing the presence of infectious SARS-COV-2 in nasopharyngeal swab specimens and sputum even at day 111, but not in saliva, urine, blood, or stool. Experiments were carried out using viral isolation by cell culture and observing the cytotoxic effects on Vero E6/TMPRSS2 cells after inoculation of the specimens into the cells, followed by the detection of viral RNA in the culture supernatant using quantitative reverse transcriptase-polymerase chain reaction (qRT-PCR) test [Abe et al., *QJM: An International Journal of Medicine* 2020, doi: 10.1093/qjmed/hcaa296].

There is a need for better treatments to decrease mucus hypersecretion. Mucus thinners, such as mucolytic agents, are inhaled medications that help thin the mucus in the airways for a person to cough it out of the lungs more easily. Mucoactive medications are intended to increase the ability to expectorate sputum or decrease mucus hypersecretion.

Mucolytic medications degrade polymer gels. They may reduce the number of flare-ups that people with chronic obstructive pulmonary disease (COPD) and chronic bronchitis have Cazzola et al., *COPD: Journal of Chronic Obstructive Pulmonary Disease* 2017, volume 14, issue 5, pages 552-563; doi: 10.1080/15412555.2017.1347918; Bianco et al., *Life* 2022, 12, 1824; doi:10.3390/life12111824]. It has been described that mucus-penetrating nanocarriers containing proteolytic enzymes may be of importance in breaking down the internal structure of mucus glycoproteins [Pangua et al., *Theory and Applications of Nonparenteral Nanomedicines* 2021, Chapter 7, pages 137-152; doi: 10.1016/B978-0-12-820466-5.00007-7].

It is desirable to provide an improved method and system to forge better accessibility of antigenic viral proteins and/or other viral constituents, or pathogenic microorganism, or toxic materials that may be sheltered, hidden, or masked within a mucus network barrier, making difficult for the viral proteins to interact with a corresponding anti-spike SARS-COV-2 antibody, or other antibody or antigenic molecular entities, in a rapid lateral flow immunoassay test. It is desirable to provide an improved procedure to facilitate the identification of a potential carrier who harbor an infectious-causing agent or an infectious causing microorganism and usually suffer no symptoms of the disease, that otherwise may be interpreted as a false negative test if the antigenic viral proteins is not released from the complex sputum molecular network barrier. It is desirable to provide identification and characterization of components resulting of the cross-reactivity occurring between a plethora of antigenic epitopes or protein domains present in sputum containing commensal or pathogenic viruses and/or bacteria, such as for example derived primarily from the coronavirome, influenzavirome, or microbiota, with a human antibody raised against the SARS-COV-2 nucleocapsid protein antigen and/or the SARS-Co-V 2 spike protein antigen attached to the platform or cassette of a COVID-19 home test, based on a lateral flow chromatographic immunoassay protocol. It is desirable to provide a fast, reliable, and inexpensive test for the diagnosis of COVID-19 and other microbial infections for taking fundamental measures for the control and treatment of the disease. Therefore, a need exists for an improved sample pre-treatment extraction procedure that allows optimization of sample preparation to attain a more accurate test result and permitting many pathogen antigens to be detected simultaneously in a single and highly multiplexed broad assay. It is also desirable to provide a system and method for degrading excess amounts of mucus in patients and which may be combined with mucolytic agents.

SUMMARY OF THE INVENTION

In one aspect, the present invention provides an improved method and system for exposing hidden or masked antigenic sites of viral specimens present in biological fluids using a home-based COVID-19 rapid lateral flow immunoassay antigen test.

In another aspect, the present invention provides and improved extraction buffer system containing one or more detergents or surfactants and one or more digestive enzymes, capable of lysing and disrupting membranes, envelopes, biofilms, or coating surfaces surrounding the virus and to extract and cleave proteins and other cellular or viral components present in sputum or phlegm or other dense mucus or gel-like biopolymer-containing structures or substances of individuals who harbor an infection-causing agent or an infection causing microorganism.

In yet another aspect, the present invention facilitates the binding of an antigenic part of a microbial protein or peptide extracted from a biological fluid with a corresponding antibody to generate an antigen-antibody complex using a lateral flow immunoassay platform or cassette format.

Another aspect of the present invention is to make visible a colored band corresponding to a complex formed with an immobilized antibody present in a conventional lateral flow immunoassay platform or cassette format, or any other modified platform or cassette format, with an extracted antigenic peptide which otherwise will not be visible.

In an additional aspect, the present invention provides an immunoassay for sputum specimens for the presence of cross-reactant moieties or epitopes of the virome and/or microbiome of the lower respiratory tract where major differences have been found between patients with pulmonary diseases and healthy individuals.

In yet another aspect of the present invention is to provide an improved method and system which can be used with biosamples other than sputum, saliva, or materials obtained from nasal, nasopharyngeal, and oropharyngeal specimens, including, but not limited to, components extracted from whole blood, serum, plasma, synovial fluid, lavage fluids, vaginal or urethral secretions, tissue biopsies, cerebrospinal fluid, amniotic fluid, urine, tears, sweat or transdermal exudates skin, nails, feces, hair, and hair follicles.

Tests were performed using commercially available COVID-19 at-home antigen-based rapid diagnostic tests including a platform or cartridge specifically for the detection of SARS-CoV-2 nucleocapsid protein antigen, one of the most produced proteins of the SARS-COV-2 virus. In the method of the present invention, one or more digestive enzymes are added to a collected biosample, in particular sputum, before testing of the biosample with the platform or cartridge to expose hidden or masked antigenic sites of the coronavirus or cross-reactant antigenic sites of related or non-related viruses or some of the plethora of epitopes generated by the microbiota to accomplish an optimal binding to an antibody used in the diagnostic test. The method of the present invention is capable of enhancing detection sensitivity by making visible a test band in the platform or cartridge when testing sputum, that otherwise will not be seen and consequently may generate a false negative result. Although tests were performed using commercial platforms, with antibodies directed to SARS-COV-2 nucleocapsid antigen, the method of the present invention can be used for any other pathogen using antibodies directed to the key antigens present in the pathogen of interest.

Samples were collected separately and independently in a less invasive, less intrusive sample collection procedure. Collection of anterior nasal-nasopharyngeal swab specimens were performed using a disposable sterile nasal swab provided by the COVID-19 antigen home test kit obtained from three suppliers (ACON Laboratories, Inc., San Diego, California, U.S.A.; iHealth Labs, Inc., Sunnyvale, California, U.S.A; Roche Diagnostics, Indianapolis, Indiana, U.S.A). The swab was introduced into the nostril as instructed by the manufacturer protocol, followed by the insertion of the swab into a tube containing an extraction buffer containing a detergent. After the appropriate extraction procedure, three to four drops of the solution of the extracted material were gently applied to the sample well of the platform or cassette provided by a test kit of the respective manufacturer, and a lateral flow chromatographic migration was allowed for the COVID-CoV-2 antigens to bind to the corresponding antibodies present in the corresponding area of the platform or cassette format. Each procedure was carried out at room temperature of about 25-degree Celsius, as instructed by the manufacturer of the corresponding test kit used.

The present invention includes a modified protocol using an extraction buffer or solution composed of a non-ionic detergent, such as for example Triton X-100 and/or Nonidet P-40 (obtained from Santa Cruz Biotechnology, Inc., Dallas, Texas, U.S.A.), at a concentration ranging from about 0.1% to about 2%, preferably about 1%, of total volume of a collected sputum specimen in a phosphate-buffered saline solution, and in the presence of at least a proteolytic enzyme and/or other polymeric digestive enzymes such as lipases and nucleases. Suitable proteolytic enzymes include one or more of Alcalase, trypsin, hyaluronidase and amylase added as a soluble enzyme in an amount ranging from about 0.1% to about 10% of total volume of a collected sputum specimen. The sputum sample can be suspended in the detergent-containing solution, or the sputum sample can be suspended in the detergent-containing solution adding the individual enzyme immobilized to polymeric or glass beads, as free-floating beads or immobilized to the inner surface of a collecting tube. The protocol related to the incubation of the mixture containing sputum, detergent and one or more digestive enzymes was performed at about 25 degrees Celsius, about 45 degrees Celsius and about 60 degrees Celsius for a period of about 15 minutes, about 1 hour, about 2 hours, about 3 hours, and about 20 hours.

The samples tested were self-collected from nasal, nasopharyngeal, oropharyngeal, and buccal swabs; as well as from saliva, sputum, and saline mouth/gargle specimens. Additional experiments were performed with trypsin, pronase, proteinase K, thermophilic proteinase, as well as amylase, and hyaluronidase, and a mixture of these enzymes obtained from commercial sources including Sigma-Aldrich, St. Louis, Missouri, U.S.A.; Worthington Biochemical Corporation, Lakewood, New Jersey, U.S.A.; Alfa Aesar Materials Company, Tewksbury, Massachusetts, U.S.A.; Thermo-Fisher Scientific, Waltham, Massachusetts, U.S.A. The sample collections were performed on persons suffering of some of the symptoms reported in a COVID-19 patient. In one testing scenario, examination by an emergency medical doctor of a local Urgent Care Clinic concluded that it may be a seasonal flu rather than COVID-19. Collection of nasopharyngeal and oropharyngeal samples of the patient by the emergency medical doctor, using a swab, were subjected to a rapid antigen test performed at the same Urgent Care Clinic, and a polymerase chain reaction (PCR) test that was sent to a specialized clinical laboratory. The result for both tests were reported negative. On the same day of the medical examination by the emergency medical doctor, but at a different laboratory, buccal, nasopharyngeal, and oropharyngeal samples were swab-independent self-collected, as well as saliva, saline mouth rinse-gargle, and sputum. All samples were analyzed by the rapid antigen test, using the flow lateral immunoassay technique, but employing the modified protocol of the present invention described above. The results on all collected samples were negative, except on the sputum sample that was clearly positive. Further time analysis was carried out every week for three months, in all swabs independent self-collected samples, and only the sputum sample resulted as positive, however the intensity of the band diminished as time progressed.

The present invention includes a disease detection system, comprising: platform or cassette to perform an antigen home test using a rapid lateral flow chromatographic immunoassay (LFIA) test intended for the qualitative detection of the nucleocapsid protein antigen from SARS-COV-2 in collected sputum specimens disrupted by the proteolytic enzyme Alcalase to release its content and digest its proteins.

The method and system of the present invention has low manufacturing costs and is inexpensive and can be performed at home as a rapid self-testing diagnostic test, regardless of the vaccination status of a person and whether or not a person has symptoms. Testing SARS-COV-2 antigen(s) in sputum using the method and system of the present invention can be rapid, very accurate, and significantly more inexpensive than other conventional tests for the presence of the coronavirus or using antibodies, nanobodies, aptamers, and/or lectins for any other pathogens.

In one embodiment, the present invention is directed to a system and method of using a proteolytic enzyme, such as Alcalase, incorporated or immobilized into a nanocarrier by itself, or in combination with other mucolytic agents, for treating a disease by degrading excess amounts of mucus in patients with chronic obstructive pulmonary disease (COPD), chronic bronchitis, and other respiratory diseases, including COVID-19.

BRIEF DESCRIPTIONS OF THE DRAWINGS

Figure 4:
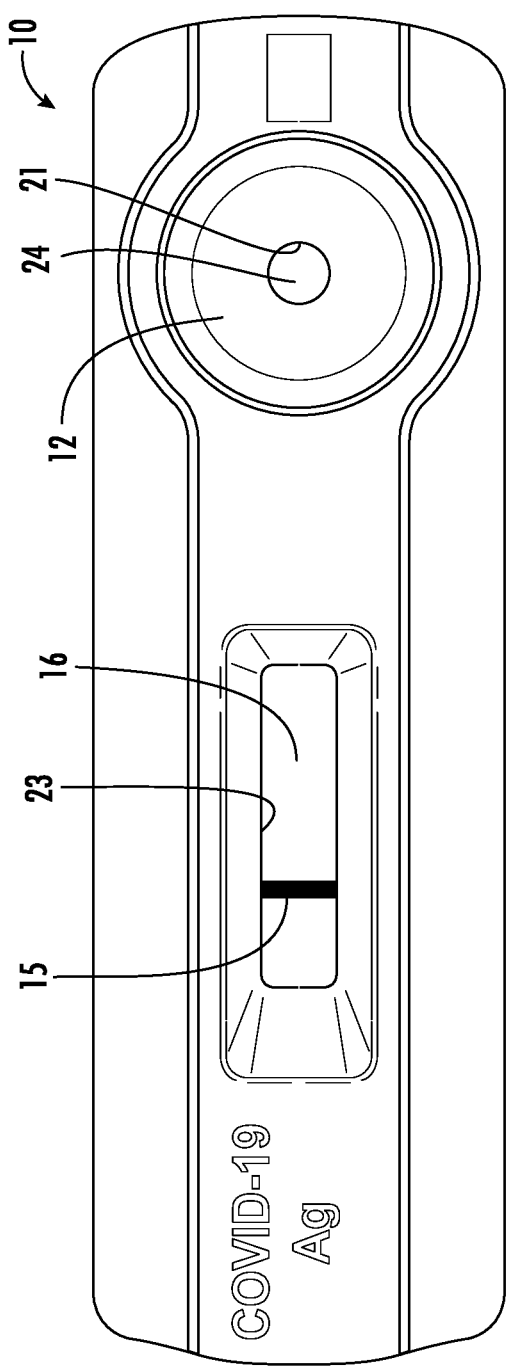

FIG. 4 is a diagrammatic perspective view that illustrates an embodiment of a platform used when performing a rapid test based on lateral flow immunoassay technique following manufacturers' protocol for a saliva sample and showing a negative test for COVID-19. Identical results were obtained when using a gargle collected specimen following the same collecting procedure for saliva and showing a negative test for COVID-19.

Figure 5:
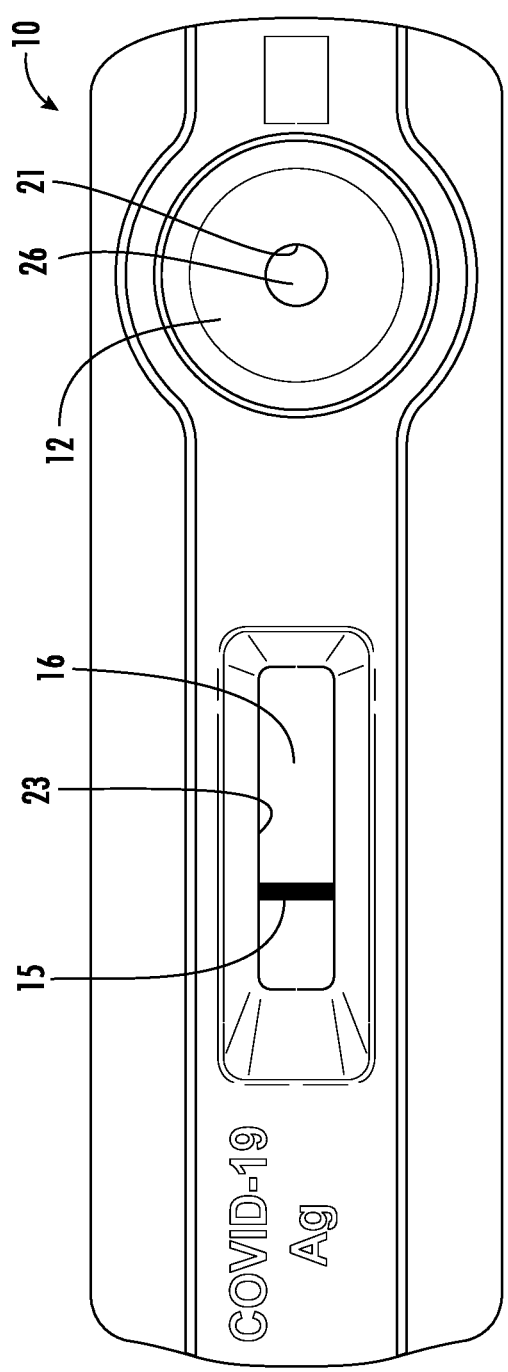

FIG. 5 is a diagrammatic perspective view that illustrates an embodiment of a platform or cartridge used when performing a rapid test based on lateral flow immunoassay technique following manufacturers' protocol for a swab sample obtained from the buccal area and showing a negative test for COVID-19.

Figure 6A:
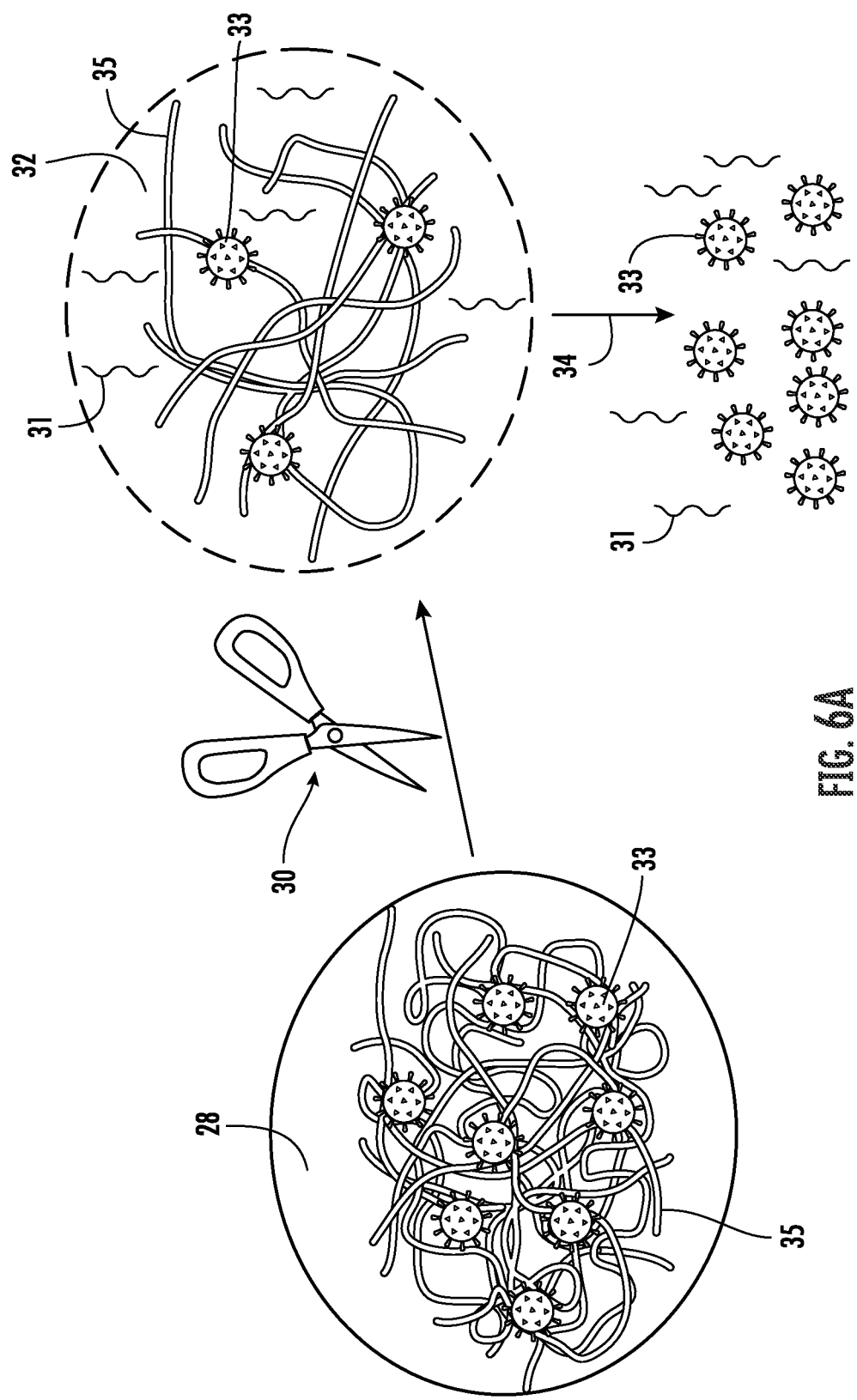

FIG. 6A is a diagrammatic perspective view that illustrates an embodiment of a method to release pathogens and material trapped within a sample of collected sputum or phlegm, using a pre-treatment lysis-extraction solution.

Figure 6B:
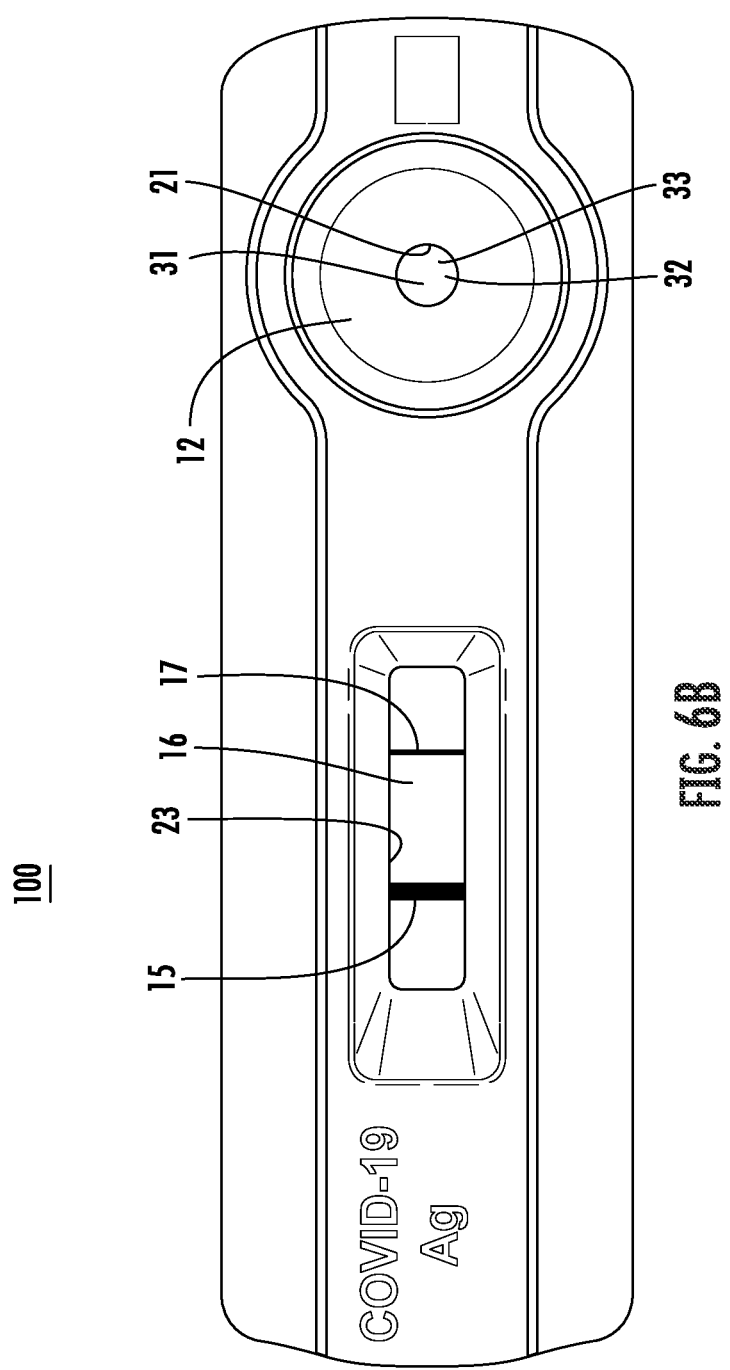

FIG. 6B is a diagrammatic perspective view that illustrates an embodiment of a disease detection system of the present invention including a platform or cartridge used when performing a method of the present invention of a rapid test based on lateral flow immunoassay for the sputum sample shown in FIG. 6A and showing a positive test for COVID-19. Release of viral components trapped within a complex meshwork barrier is crucial for the interactions of the corresponding antibodies present in the LIFT platform or cassette.

Figure 7D:
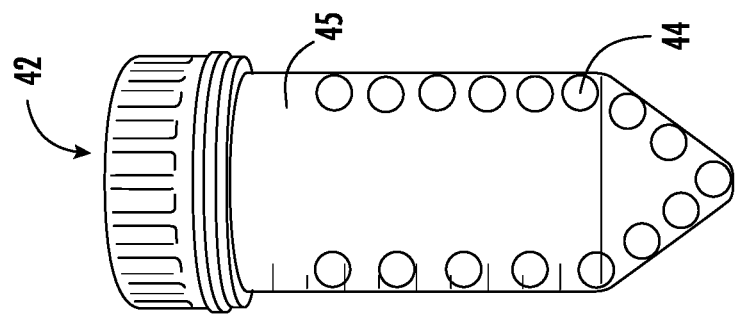
Figure 7C:
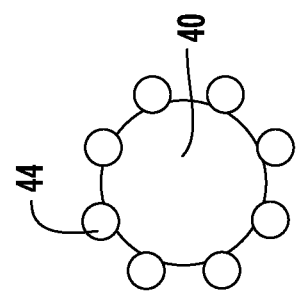
Figure 7B:
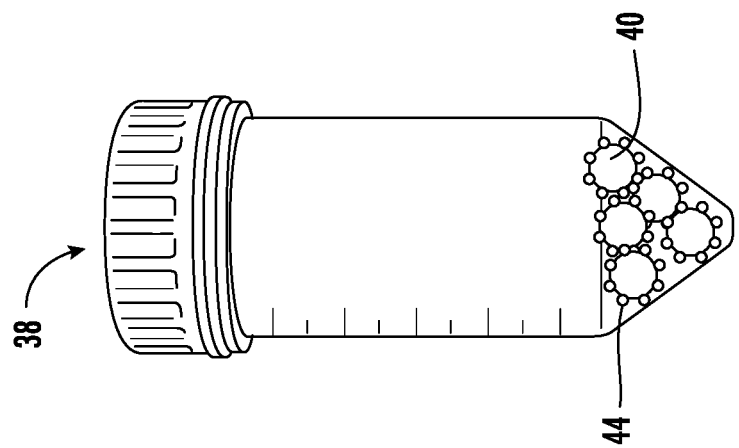
Figure 7A:
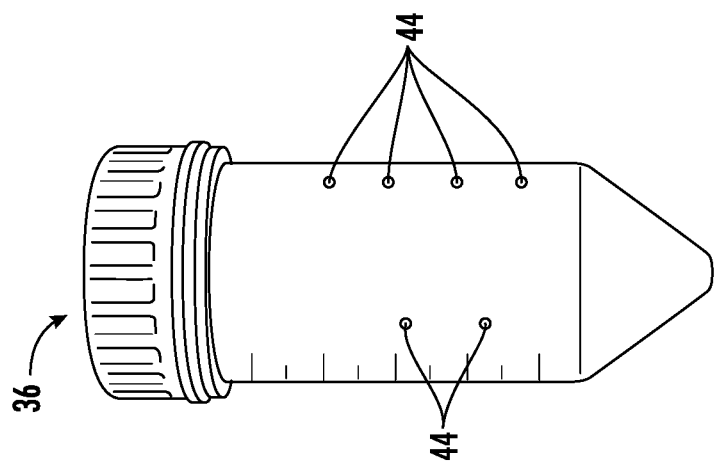

FIG. 7A is a diagrammatic representation of collection tube to collect sputum in a detergent-containing solution in the presence of one or more free-solution digestive enzymes.

FIG. 7B is a diagrammatic representation of collection tube to collect sputum in a detergent-containing solution in the presence of one or more digestive enzymes immobilized to free-floating beads used as a solid support.

FIG. 7C is a diagrammatic representation of a polymeric or glass beads containing one or more digestive enzymes immobilized to their surfaces used as a solid support.

FIG. 7D is a diagrammatic representation of collection tube to collect sputum in a detergent-containing solution in the presence of one or more digestive enzymes immobilized to an inner surface of the collection tube used as a solid support.

Figure 7E:
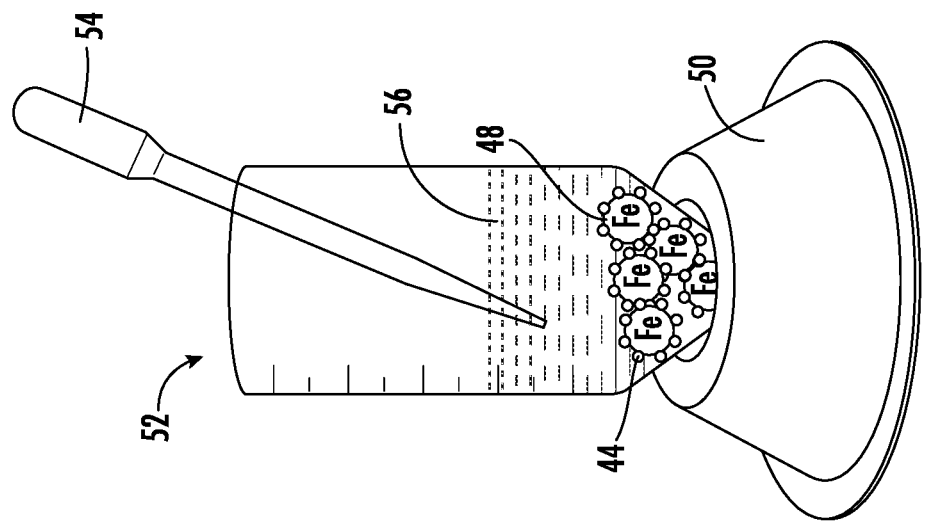

FIG. 7E is a diagrammatic representation of a high-binding capacity magnetic beads containing one or more digestive enzymes immobilized to their surfaces, used as a solid support, and standing on a magnet that serves as a base support and for decanting the magnetic beads.

Figure 7F:
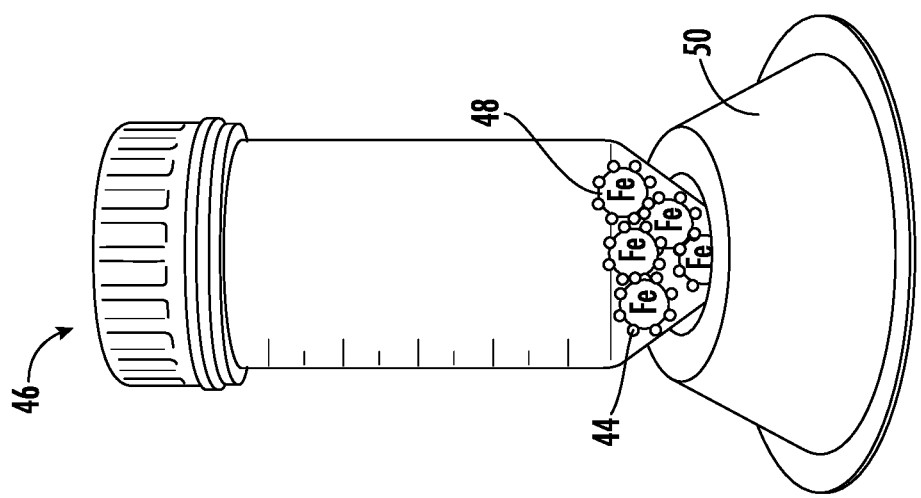

FIG. 7F is a diagrammatic representation of a high-binding capacity magnetic beads containing one or more digestive enzymes immobilized to their surfaces, used as a solid support, and standing on a magnet that serves as a base support and for facilitating the decanting of the magnetic beads to the bottom of the tube in a short period of time. The supernatant containing the lysed-extracted viral particles and/or their components can be removed by a disposable transfer plastic tube, to further apply a few drops of the mixture into the sample well of a lateral flow immunoassay platform or cassette.

Figure 8:
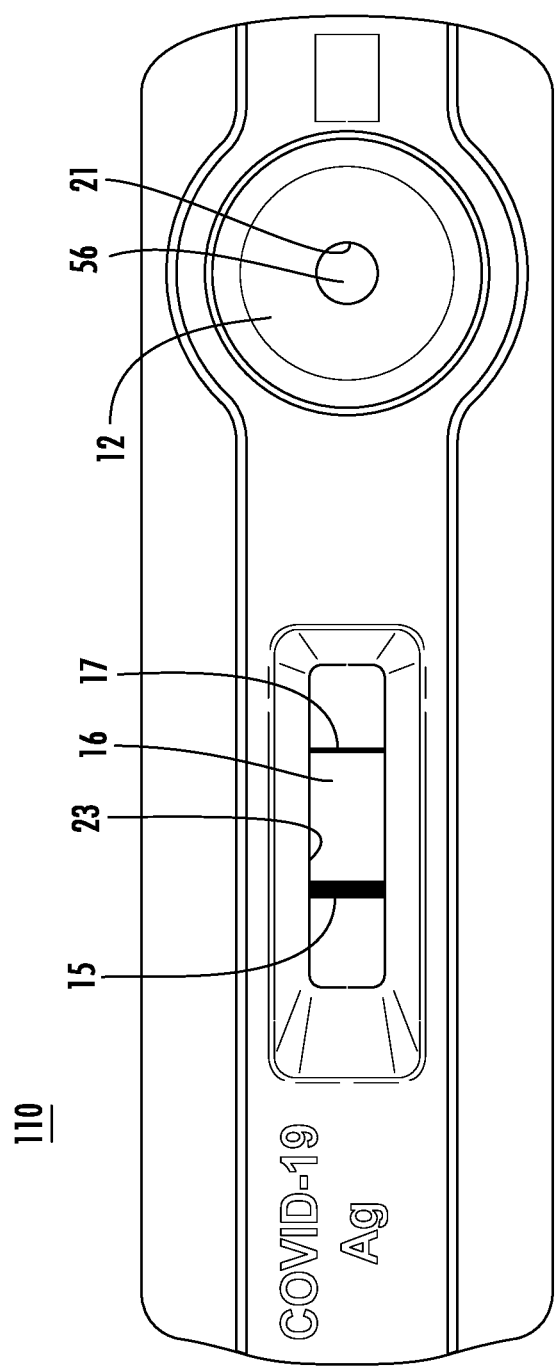

FIG. 8 is a diagrammatic perspective view that illustrates an embodiment of a disease detection system including a platform or cartridge used when performing a rapid test based on lateral flow immunoassay technique and a modified method of the present invention including pre-treating a sputum sample and showing a positive test for COVID-19. The pre-treatment of the sputum sample comprised the steps of adding to a collected sputum sample in a sterile container, a detergent solution, and a free-solution proteolytic enzyme, such as Alcalase, followed by a 15-minute incubation time at room temperature.

Figure 9:
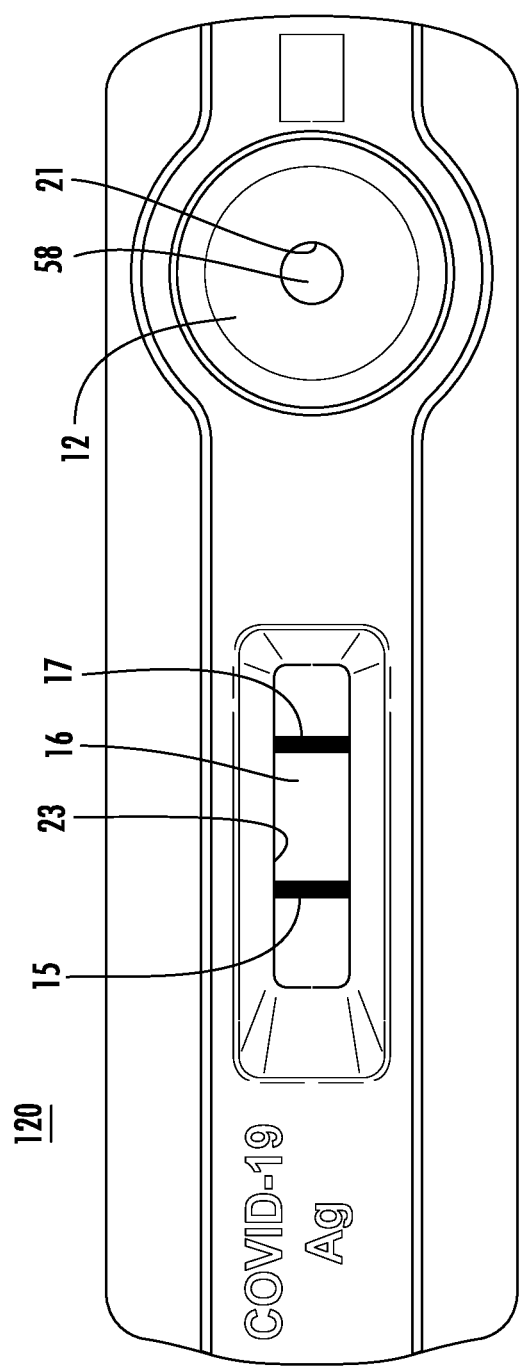

FIG. 9 is a diagrammatic perspective view that illustrates an embodiment of a disease detection system including a platform or cartridge used when performing a rapid test based on lateral flow immunoassay technique and a modified method of the present invention including pre-treating a sputum sample and showing a positive test for COVID-19. The pre-treatment of the sputum sample comprised the steps of adding to a collected sputum sample in a sterile container, a detergent-containing solution, and a free-solution proteolytic enzyme, such as Alcalase, followed by a one-hour incubation time at room temperature.

Figure 10:
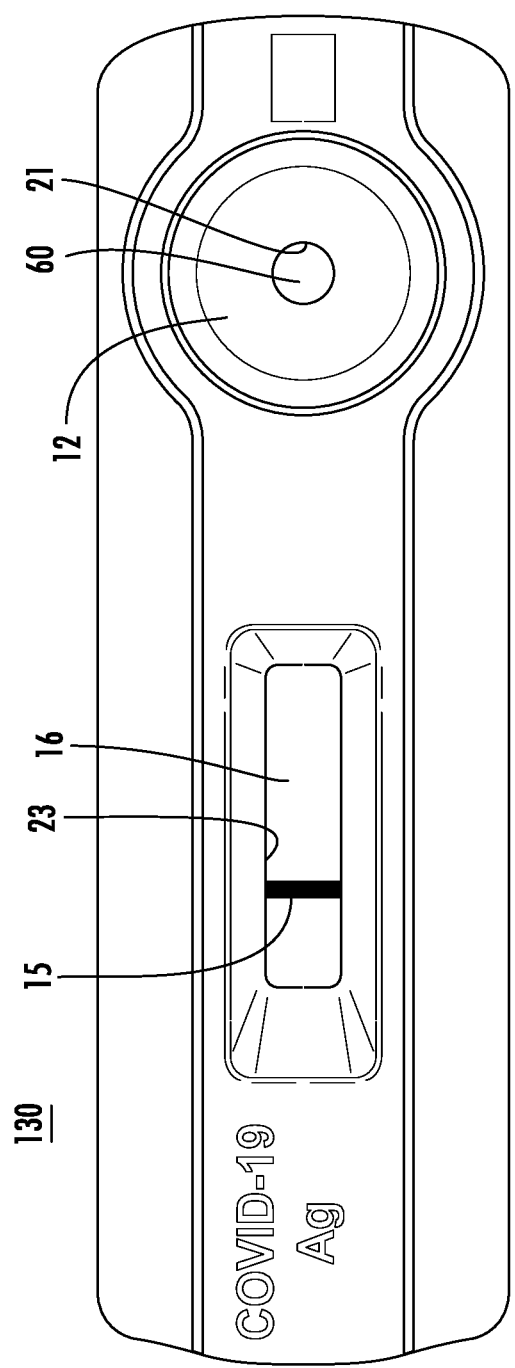

FIG. 10 is a diagrammatic perspective view that illustrates an embodiment of a disease detection system including a platform or cartridge used when performing a rapid test based on lateral flow immunoassay technique and a modified method of the present invention including pre-treating a swab sample obtained from the nostrils or external openings of the nasal cavity and showing a negative test for the presence of SARS-COV-2 virus. The pre-treatment of the nasal sample comprised the steps of adding the swab-containing nasal material to a detergent-containing solution, and a free-solution proteolytic enzyme, such as Alcalase, followed by a one-hour incubation time at room temperature.

Figure 11:
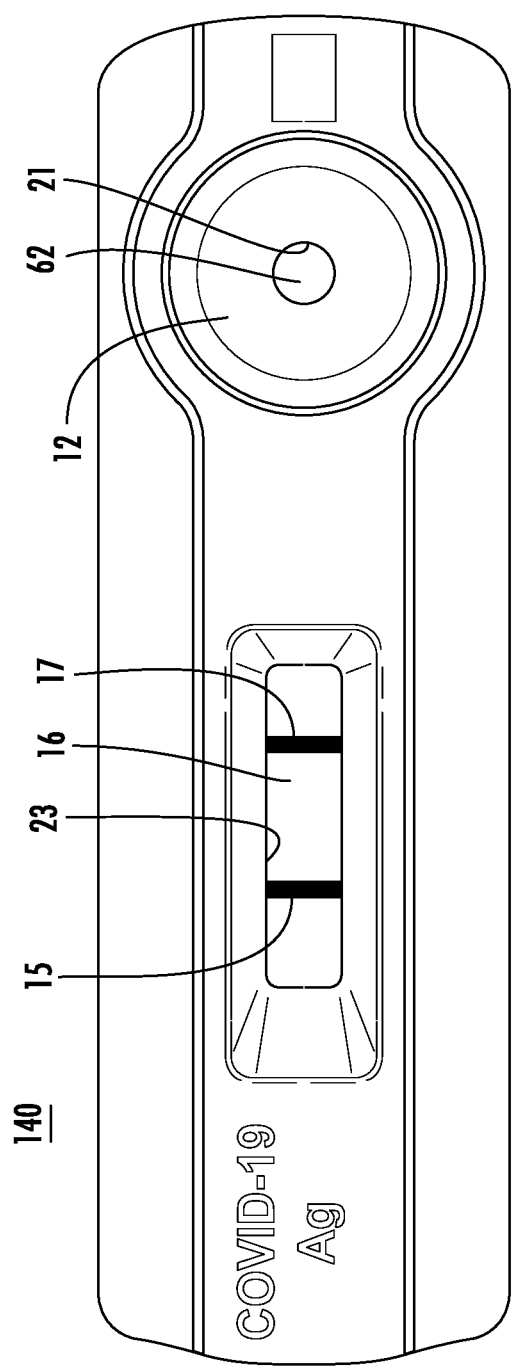

FIG. 11 is a diagrammatic perspective view that illustrates an embodiment of a disease detection system including a platform or cartridge used when performing a rapid test based on lateral flow immunoassay technique and a method of the present invention including pre-treating a sputum sample with a detergent-containing solution and a free-solution proteolytic enzyme (Alcalase) and showing a positive test for the presence of SARS-COV-2 virus. The pre-treatment of the sputum sample comprised the steps of adding to a collected sputum sample in a sterile container, a detergent solution, and a free-solution proteolytic enzyme, such as Alcalase, followed by two-hours incubation time at room temperature.

Figure 12:
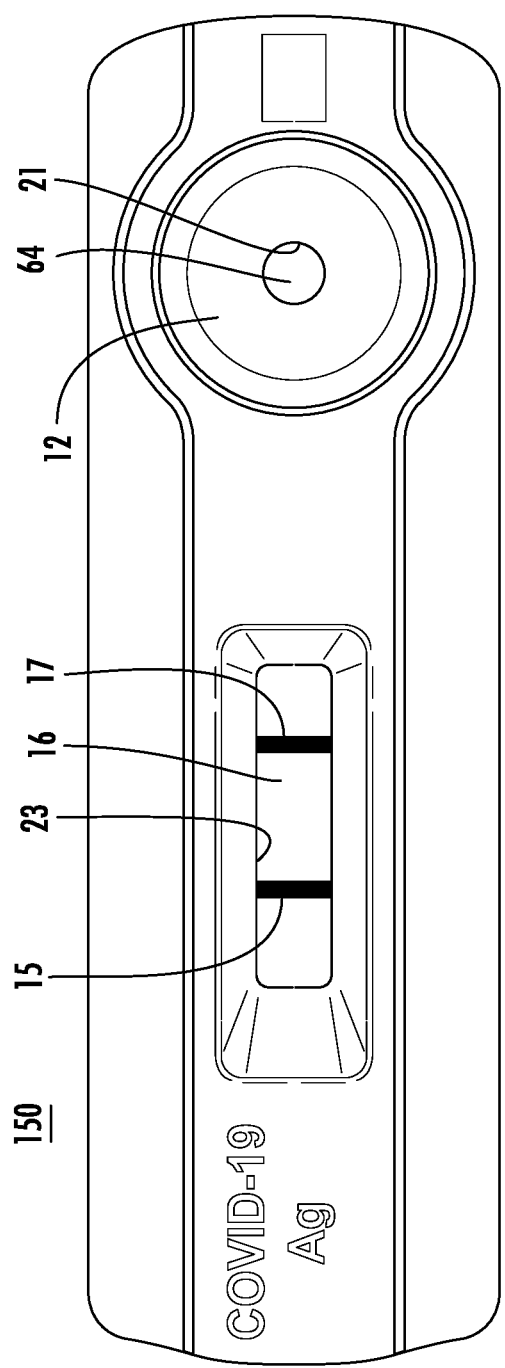

FIG. 12 is a diagrammatic perspective view that illustrates an embodiment of a disease detection system including a platform or cartridge used when performing a rapid test based on lateral flow immunoassay technique and a method of the present invention including pre-treating a sputum sample with a detergent-containing solution and an immobilized proteolytic enzyme, such as Alcalase, on free floating-beads and incubation for two-hours at room temperature and showing a positive test for COVID-19.

Figure 13:
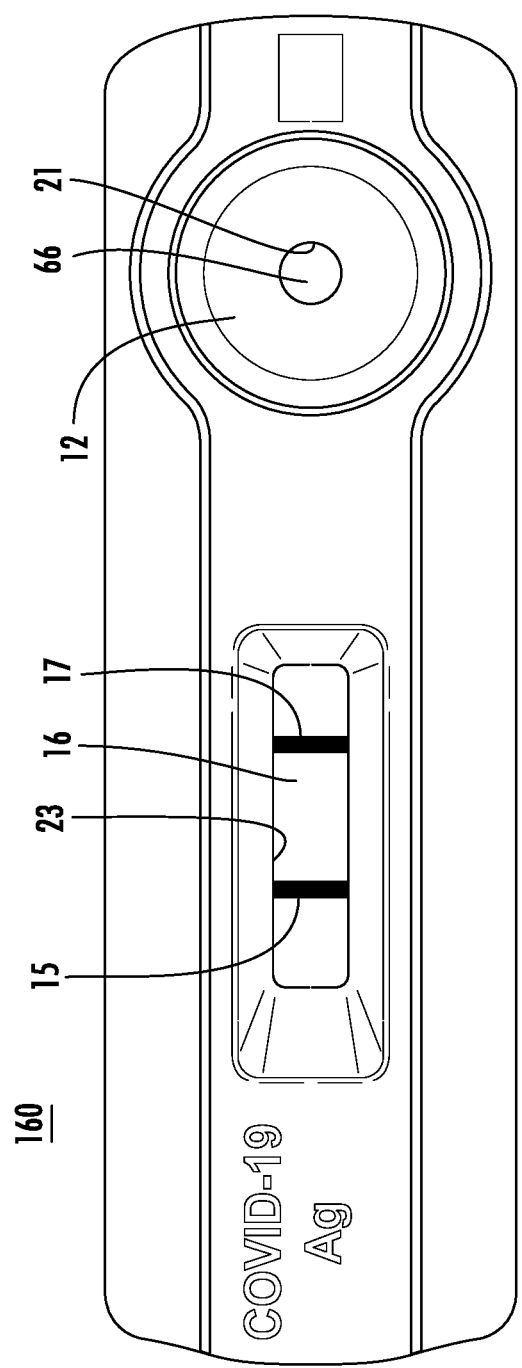

FIG. 13 is a diagrammatic perspective view that illustrates an embodiment of a disease detection system including a platform or cartridge used when performing a rapid test based on lateral flow immunoassay technique and a method of the present invention including pre-treating a sputum sample with a detergent-containing solution and a mixture of free-solution proteolytic enzyme, such as Alcalase, hyaluronidase, and amylase, and incubation for two hours at room temperature and showing a positive test for COVID-19.

Figure 14:
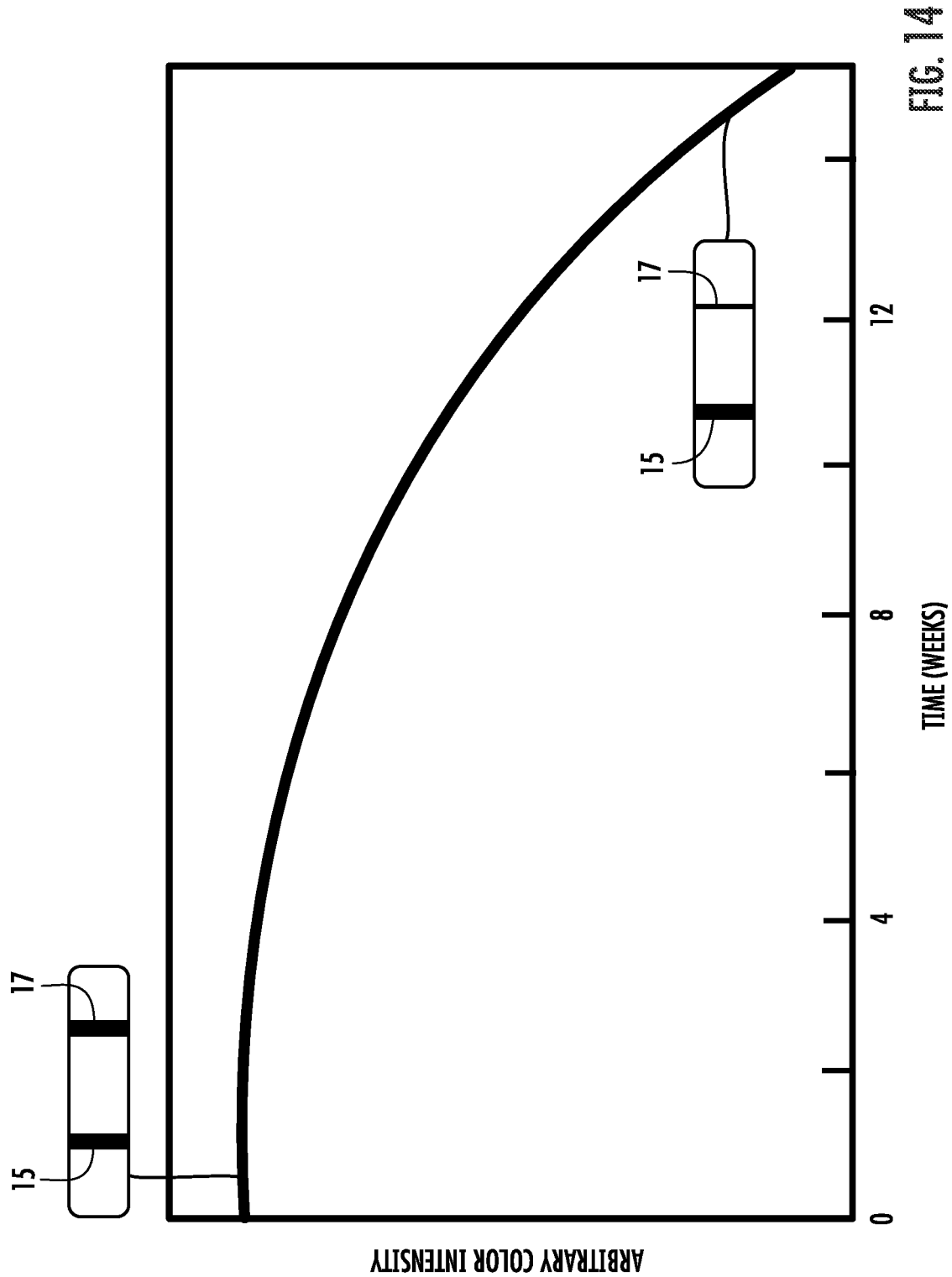

FIG. 14 is a graphical plot that illustrates results of a time experiment when performing a rapid test based on lateral flow immunoassay technique and a method of the present invention including pre-treating a sputum sample in a detergent-containing solution and a free-solution proteolytic enzyme, such as Alcalase, followed by incubation for about two hours at room temperature, collected separately and independently, once a week for 12 weeks and showing a positive test for the presence of SARS-COV-2 virus.

DETAILED DESCRIPTION

Reference will now be made in greater detail to a preferred embodiment of the invention, an example of which is illustrated in the accompanied drawings. Wherever possible, the same reference numerals will be used throughout the drawings and the description to refer to the same or like parts.

Figure 1:
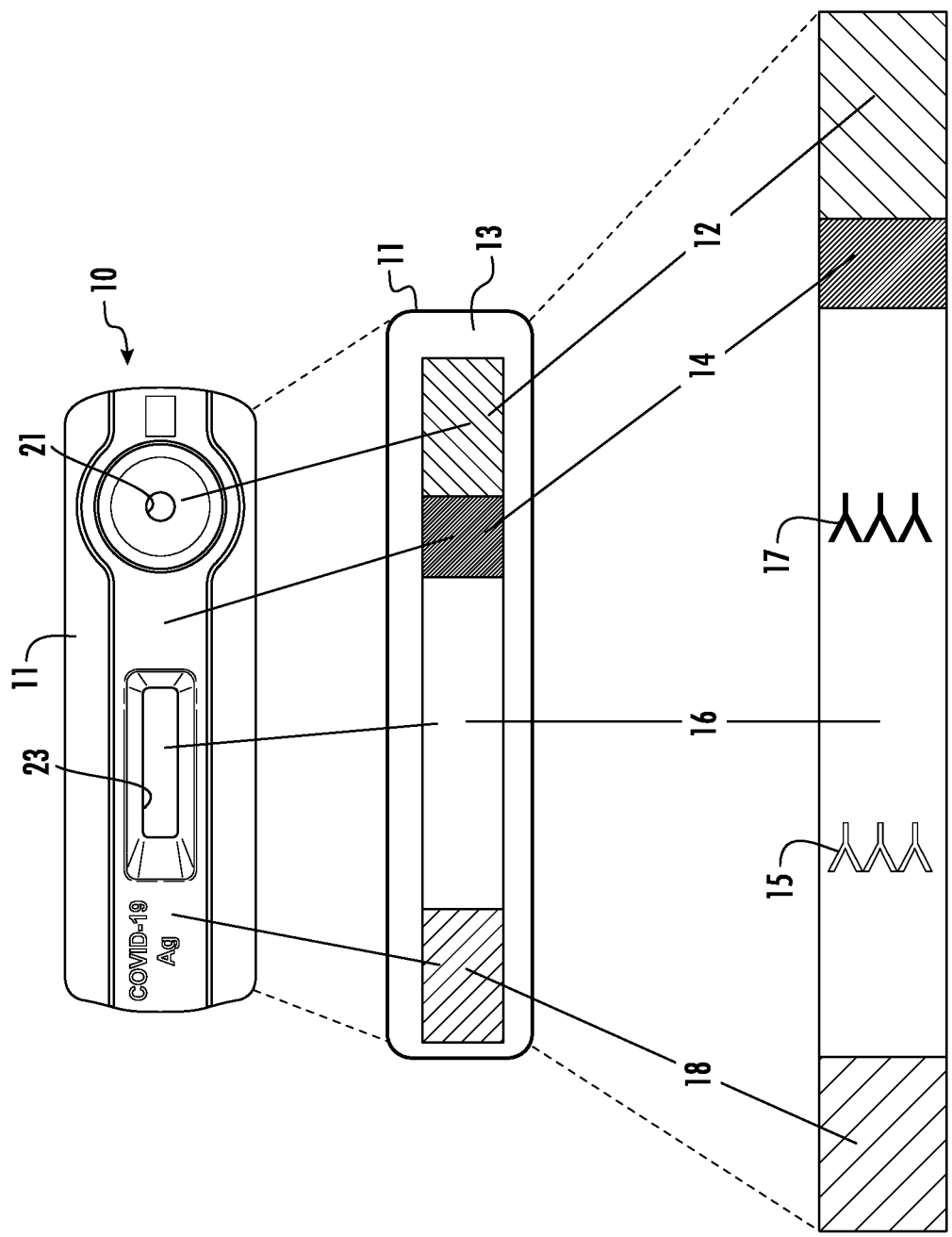
FIG. 1 is a schematic diagram of components embodied in a prior art technique known as lateral flow chromatography immunoassay.

FIG. 1 illustrates a representation of prior art platform or cassette of immunoassay test, known as a "lateral flow immunoassay/immunochromatography technique" or simply lateral flow immunoassay (LFIA). LFIA is point-of-care antigen test design that is inexpensive, rapid, and easy to use. In the LFIA technique there is movement of liquid, or its extracts containing an analyte of interest, such as an antigen, along a strip of a polymeric material thereby passing various zones where molecules, such as antibodies, have been attached and can exert, more or less, specific interactions with the analyte.

Platform or cartridge 10 includes four main components: sample application pad 12, conjugate pad 14, migration membrane pad 16, and adsorbent pad 18. Sample application pad 12, conjugate pad 14, migration membrane pad 16, and adsorbent pad 18 can be integral to one another to form respectfully a sample application zone, a conjugate zone, a migration zone, and an adsorbent zone. Suitable platforms or cartridges having features which can be used in the present invention have been described in publications referring to various platforms used in LFIA tests [Wong R. C., Tse H. Y. (Eds.), Lateral Flow Immunoassay, Humana Press, a part of Springer Science-Business Media LLC, New York, New York 2009; doi: 10.1007/978-1-59745-240-3; Sajid et al., *Journal of Saudi Chemical Society* 2015, volume 19, pages 689-705; Posthuma-Trumpie et al., *Analytical and Bioanalytical Chemistry* 2009, volume 393, pages 569-582; Babu et al., U.S. Pat. No. 9,121,849, Sep. 1, 2015; Kabir et al., U.S. Pat. No. 8,399,261, Mar. 19, 2013; Kamei et al., U.S. Patent Publication Number 2020/0033336, Dec. 28, 2021; Patriquin et al., *Microbiology Spectrum* 2021, volume 9, e00683-21; doi: 10.1128/Spectrum.00683-21; Zhou et al., *Trends in Analytical Chemistry* 2021, volume 145, 116452; doi: 10.1016/j.trac.2021.116452; Andryukov, *AIMS Microbiology* 2020, volume 60, issue 3, pages 280-304; doi: 10.3934/microbiol.2020018]. Each of these publications is incorporated by reference into this application.

Migration membrane pad 16 can be formed of a polymeric material which is often thin and fragile. The polymeric material forming migration membrane pad 16 can be attached to a plastic or nylon basic layer for stability to allow cutting and handling. In one embodiment, migration membrane pad 16 is a nitrocellulose membrane. Sample application pad 12, conjugate pad 14, migration membrane pad 16, and adsorbent pad 18 can be housed in housing 11 on inner surface 13 of housing 11. Sample application pad 12 is exposed through window 21 of housing 11. Migration membrane pad 16 is exposed through window 23 of housing 11. Points of antigen-antibody reactions are visualized by band 15 and band 17 on migration membrane pad 16. Housing 11 provides robustness. Housing 11 can be formed of plastic. Platform or cartridge 10 can be produced from nitrocellulose, nylon, polyethersulfone, polyethylene, cellulose acetate or fused silica glass, and combinations of these materials.

Band 15 can be referred to as a Control band, or C band. Band 17 can be referred to as a Test band, or T band. Band 15 as a Control band can be precoated with an antibody that is not from human sources. For example, the antibody can be from chicken or other species, such as chicken IgY. Band 17 as a Test band can be precoated with an anti-SARS-Co-2 specific antibody.

Sample application pad 12 can be a sample well where a buffer processed-lysed-extracted sample is applied. As migration occurs, by capillary action, constituents of the processed-extracted sample in the buffer flow progressively through platform or cassette 10, and sequentially flow through sample application pad 12, conjugate pad 14, migration membrane pad 16, and eventually to adsorbent pad 18. Adsorbent pad 18 can act as a wick. At migration membrane pad 16 interaction with a corresponding latex fluorescence microsphere or gold-conjugated chicken IgY and latex fluorescence microspheres or gold nanospheres-conjugated human IgG specific to SARS-COV-2 can occur. In the absence of SARS-COV-2 antigen, for example nucleoprotein (N) protein, membrane (M) protein or envelope (E) protein, in the processed-extracted sample, the conjugated anti-SARS-COV-2 antibody will not interact with the anti-SARS-COV-2 capture antibody at band 17 as a Test band.

Band 15 as a Control band and band 17 as a Test band can be formed in color when the sample applied to sample application pad 12 tested positive for SARS-COV-2 infection. Positive results indicate the presence of viral antigens. Clinical correlation with patient history and other diagnostic information is needed to determine infection status. Positive results do not rule out bacterial infection or co-infection with other viruses. Band 15 as a Control band can be formed in color and band 17 as a Test band is not formed in color when the sample applied to sample application pad 12 tested negative. Negative results are presumptive, and confirmation with a molecular assay, if necessary for patient management, may be performed.

Figure 2:
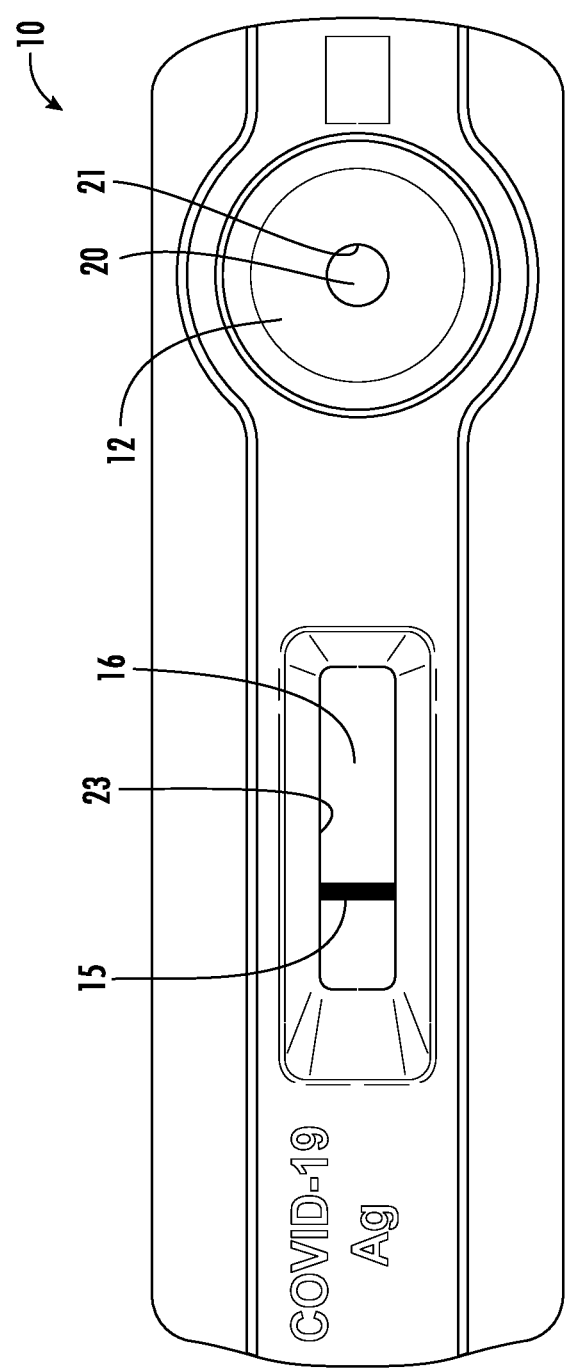
FIG. 2 is a diagrammatic perspective view that illustrates an embodiment of a platform or cartridge used when performing a rapid test based on lateral flow immunoassay technique following manufacturers' protocol for a swab sample obtained from the nostrils or external openings of the nasal cavity and showing a negative test for COVID-19.

FIG. 2 illustrates results of nasopharyngeal sample 20 tested using platform or cartridge 10 and a lateral flow immunoassay (LFIA) test. A nasal swab sample was self-collected by a patient suspected of carrying the SARS-COV-2 virus, using a protocol indicated by the manufacturer, and using all components provided in the kit, the kit was manufactured by Acon Laboratories, Inc., San Diego, California, U.S.A. Other kits were used as well to confirm results, and they were obtained from iHealth Labs, Inc., Sunnvale, California, U.S.A.; Roche Diagnostics, Indianapolis, Indiana, U.S.A. A sterile swab of the kit was used, and the entire absorbent tip of the swab head was gently inserted into one nostril (about ½ to ¾ of an inch). The swab was firmly rub in a circular motion around the inside wall of the nostril 5 times for about 15 seconds. Then, the same procedure was applied to the second nostril. The swab was removed from the nostril and immediately placed into a tube of the kit containing an extraction buffer. The swab was swirled 5 times for about 30 seconds while squeezing the provided plastic tube to extract as many constituents as possible into the extraction buffer to form nasopharyngeal sample 20. The swab was discarded into the trash. Once the extracted nasopharyngeal sample 20 was mixed completely, approximately 3 to 4 drops of nasopharyngeal sample 20 was dispensed into sample application pad 12 being formed as a well. The migration of nasopharyngeal sample 20 by capillarity was allowed and a reading of appearance of band 15 as a Control band having a color was performed at about 15 minutes. Band 17 as a Test band did not appear in color as shown in FIG. 2. The test resulted in a negative value for the detection of SARS-COV-2 virus, using nasopharyngeal sample 20 obtained from the nostrils.

Figure 3:
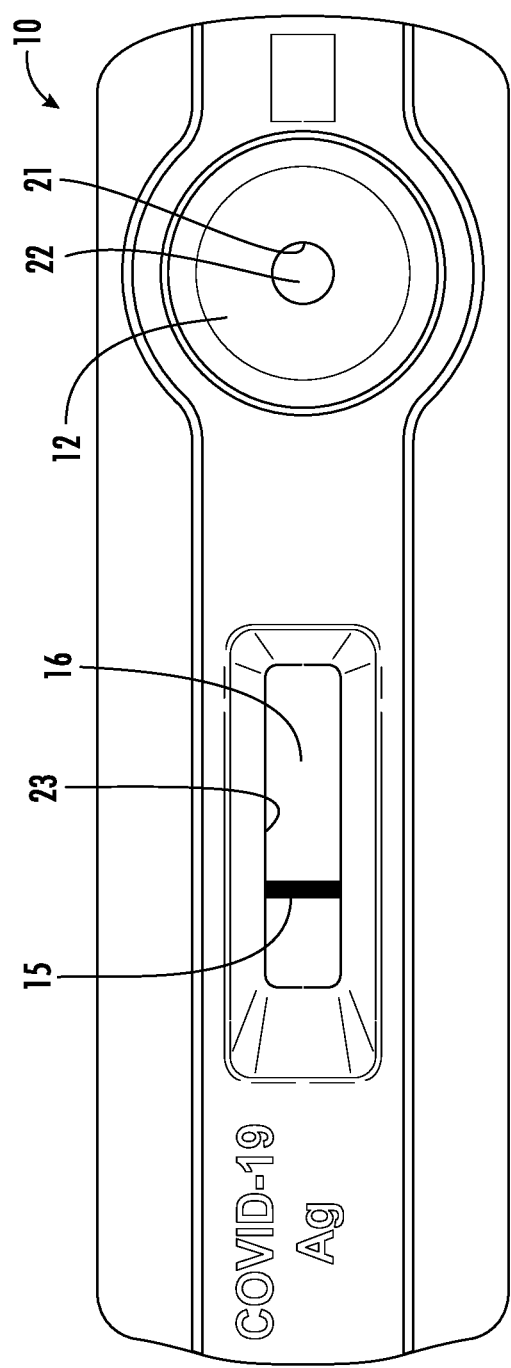
FIG. 3 is a diagrammatic perspective view that illustrates an embodiment of a platform or cartridge used when performing a rapid test based on lateral flow immunoassay technique following manufacturers' protocol for a swab sample obtained from the oropharyngeal area and showing a negative test for COVID-19.

FIG. 3 illustrates results of oropharyngeal sample 22 tested using platform or cartridge 10 and using the lateral flow immunoassay (LFIA) test. A throat sample was self-collected by a patient suspected of carrying the SARS-COV-2 virus, using the entire protocol indicated by the manufacturer, as described above with regard to FIG. 2 and using all components provided in the kit to form oropharyngeal sample 22. As indicated in FIG. 3, a reading of appearance of band 15 as a Control band appeared in color and band 17 as a Test band did not appear in color. The test resulted in a negative value for the detection of SARS-COV-2 virus, using oropharyngeal sample 22 obtained from the throat.

FIG. 4 illustrates results of saliva sample 24 tested using platform or cartridge 10 and using the lateral flow immunoassay (LFIA) test. A saliva sample was self-collected by a patient suspected of carrying the SARS-COV-2 virus, using a slight modification of the protocol indicated by the manufacturer, but still using all components provided in the kit, as described above with regard to FIG. 2. Saliva was collected in a first sterile tube. Once collected about 3 to 4 milliliters, 1 milliliter was transferred to a second sterile tube containing an extraction buffer, provided by the manufacturer, with a sterile plastic transfer pipette after mixing the content of the second sterile tube to form saliva sample 24. The rest of the procedure was identical, as the one described above with regard to FIG. 2. As indicated in FIG. 4, a reading of appearance of band 15 as a Control band appeared in color and band 17 as a Test band did not appear in color. The test resulted in a negative value for the detection of SARS-COV-2 virus, using saliva sample 24 obtained from saliva. Identical negative results were obtained when using a gargle collected specimen, following the same collecting procedure for saliva (not shown).

FIG. 5 illustrates results of buccal sample 26 tested using platform or cartridge 10 and using the lateral flow immunoassay (LFIA) test. Buccal sample 26 was self-collected by rubbing the inside of the cheek of a patient suspected of carrying the SARS-COV-2 virus, using the entire protocol indicated by the manufacturer, and using all components provided in the kit, as described in FIG. 2. As indicated in FIG. 5, a reading of appearance of band 15 as a Control band appeared in color and band 17 as a Test band did not appear in color. The test resulted negative for the detection of SARS-COV-2 virus, using buccal sample 26 obtained from rubbing the inside of the cheek.

FIG. 6A illustrates a method of the present invention to break down collected sputum sample 28, also known as phlegm. Collected sputum sample 28 can be expectorated sputum, or the sputum collected by induction with hypertonic saline. Sputum is gel-like mucus which is coughed up from the respiratory tract, often either following an infection or an irritation of the mucosa. Samples of sputum were collected early in the morning, before eating or drinking, after rinsing the mouth with clear water for about 15 seconds to eliminate any contaminant in the oral cavity. After expelling saliva, the patient then breathes deeply three times to cough at about 2-minutes intervals until bringing up some sputum. The sputum is then release in a sterile well-closed container. About 1 milliliter of a detergent solution of 1% of Triton X-100 or 1% Nonidet P-40 is added to about 2 to about 3 milliliters of collected sputum sample 28 in a sterile container. For example, the sterile container can be a tube. The sterile container is rotated gently using a tube rotor mixer or by hand for about 10 minutes. Then about 30 microliters of free-solution digestion enzyme 30 is added to a total volume of about 3 milliliters of collected sputum sample 28 mixed in the detergent solution, making a ratio of about 1% of enzyme-sputum solution. The concept of a digestion enzyme, also known as biological scissors or chewers have been reported in the literature [López-Otín et al., *Journal of Biological Chemistry* 2008, volume 283, issue 45, pages 30433-30437]. Digestion enzyme 30 disrupts collected sputum sample 28 to form disrupted sputum sample 32. Collected sputum sample 28 is complex and can be disrupted to a less complex open entity to form disrupted sputum sample 32. Disrupted sputum sample 32 includes large and complex polymeric glycoproteins 35 fragmented to produce small components 31 derived from large and complex polymeric glycoproteins 35 and viral species 33. Viral species 33 represents part of the microbiota of the sputum composed of several microorganisms. In one embodiment, viral species 33 can include the SARS-COV-2 virus. Aliquots of disrupted sputum sample 32 are taken at various times of mixing, at about 25-degree Celsius. Unraveling meshwork of disrupted sputum sample 32 to format 34 permits the release of fragmented small components, derived from the proteolytic process, to be analyzed by lateral flow immunoassay (LFIA) test.

Digestion enzyme 30 can comprise one or more proteolytic enzymes and/or one or more polymeric carbohydrate-digestive enzymes. Digestive enzyme 30 can be proteolytic enzyme Alcalase commercially available from Novozymes (Bagsvaerd, Denmark), or distributors such as Univar Solutions (Morresville, Pennsylvania, U.S.A.) which is derived from *Bacillus licheniformis*. A liquid food-grade of Alcalase can be used. Alcalase (Subtilisin) is an efficient protease for hydrolysis of different proteins. Alcalase is an endopeptidase which breaks peptide bonds from C-terminal amino acids. Alcalase is a versatile enzyme that can provide very extensive hydrolysis and is capable to disrupt and open the closed semi-permeable sputum complex to be able to release viral particles and/or components of the SARS-COV-2 virus and thus allowing the interaction with the respective antibodies present in a lateral flow immunoassay platform or cassette 10.

Digestion enzyme 30 can be trypsin, pronase, proteinase K, thermophilic proteinase, amylase, and hyaluronidase, and mixtures of thereof. Digestion enzyme 30 can be of the serine type with a broad specificity which perform well in alkaline conditions. It will be appreciated that various concentrations, times of incubations, and a range of temperatures can be used in accordance with the teachings of the present invention. The performance of Alcalase for sputum disruption and release of its content was the best in comparison to enzymes including trypsin, pronase, papain, proteinase K, thermophilic proteinase, amylase, and hyaluronidase, and mixtures of thereof. The cost of Alcalase is inexpensive in comparison with the other digestive enzymes. The total cost for assaying SASRS-COV-2 using the LFIA, including the platform or cassette 10, the proteolytic enzyme Alcalase and Triton X-100 can be under $12.00. Platform or cassette 10 can be used at home with minimal training.

Digestion enzyme 30 can be in solution with a detergent. The detergent can be a non-ionic detergent, ionic detergent or zwitterionic detergent. Suitable non-ionic detergents include for example Triton X-100 and Nonidet P-40. Suitable ionic detergents include for example sodium dodecyl sulfate. Suitable zwitterionic detergents include 3-(3-cholamidopropyl(dimethylammonio)-1-propane-sulfonate (CHAPS).

FIG. 6B is a diagrammatic perspective view of disease detection system 100 that illustrates results of disrupted sputum sample 32, components of large and complex polymeric glycoproteins 31 and viral species 33 tested using a platform or cartridge and using the method of the present invention based on lateral flow immunoassay (LFIA) when extracting a collected sputum sample in a container containing a detergent solution and a free-solution proteolytic enzyme Alcalase to test for the presence of SARS-COV-2 viral antigens. Approximately about 2 to about 3 drops of disrupted sputum 32 were applied to sample application pad 12, being formed as a well. As indicated in FIG. 6B, a reading of appearance of band 15 as a Control band appeared in color and Band 17 as a Test band appeared in color. The test resulted positive for the detection of SARS-CoV-2 virus, using disrupted sputum sample 32. Release of viral components trapped within a complex meshwork barrier is crucial for the interactions of the corresponding antibodies present in the lateral flow immunoassay (LFIA) platform or cassette.

FIG. 7A illustrates a method of the use of digestive enzyme 44 within a tube or container 36. Digestive enzyme 44 is free-floating within tube or container 36. Digestive enzyme 44 can be proteolytic enzyme Alcalase. FIG. 7B illustrates a method of the use of digestive enzyme 44 within a tube or container 38. Digestive enzyme 44 is immobilized to particles 40 as shown in FIG. 7C. Particles 40 can be beads. The beads can be formed of glass, other polymeric materials, or a mixture of glass and polymeric materials. Referring to FIG. 7B, particles 40 including immobilized digestive enzyme 44 can move by gravity to bottom of the tube or container 38 or by centrifugation. Digestive enzyme 44 can be proteolytic enzyme Alcalase. FIG. 7D illustrates a method of the use of digestive enzyme 44 within tube or container 42. Digestive enzyme 44 is immobilized to inner wall 45 of tube or container 42. Digestive enzyme 44 can be proteolytic enzyme Alcalase. Alternatively, magnetic beads 48 containing immobilized proteolytic enzyme 44 to their surfaces, such as Alcalase, can be retained by magnet support within tube or container 46 as shown in FIG. 7E.

FIG. 7F is a diagrammatic representation of magnetic beads 48 within tube or container 52. Tube or container 52 stands on magnet support 50 that serves as a base support and for facilitating the decanting of magnetic beads 48 to the bottom of tube or container 52 in a short period of time. Magnetic beads 48 can have a high-binding capacity. Magnetic beads 48 can comprise or be made of iron oxide carrying a functional group for attaching molecules, containing one or more digestive enzymes 44, such as Alcalase, immobilized to their surfaces, used as a solid support. Supernatant 56 containing lysed-extracted viral particles and/or their components can be removed by transfer tube 54. Transfer tube 54 can be disposable and formed of plastic. Transfer tube 54 can be used to apply a few drops of the mixture into the sample well of a lateral flow immunoassay platform or cassette.

Gravity, centrifugation, or magnet attraction can be used to separate sputum debris from supernatant containing viral particles and/or constituents of virus or other pathogenic entities. Typically, more than about 90% of a collected sputum sample is disrupted under optimized conditions, with a remaining precipitate in the bottom of tube or container 38, 46, or 52. The disruption of sputum depends on the complexity of the gel-like meshwork of the sputum. Time of interaction between the proteolytic enzyme and the sputum and the concentration of Alcalase are preferred components for obtaining optimal results.

In one embodiment, at least one detergent is contained in tube or container 36, 38, 42, 46 and 52.

In one embodiment, the present invention is directed to a system and method of using digestive enzyme 44 for disease treatment by degrading excess amounts of mucus in patients with chronic obstructive pulmonary disease (COPD), chronic bronchitis, and other respiratory diseases, including COVID-19. Digestive enzyme 44 can be used as described in any of the embodiments shown in FIGS. 7A-7F. Digestive enzyme 44 can be a proteolytic enzyme, such as Alcalase. Digestive enzyme 44 can be used in solution with at least one detergent. Digestive enzyme 44 can be used in combination with at least one mucolytic agent. Suitable mucolytic agents can include mucus thinners such as for example hypertonic saline, mannitol (Bronchitol® manufactured by Chiesi USA, Inc., Cary, North Carolina, U.S.A.), and dornase alfa (Pulmozyme® manufactured by Genentech, Inc., South San Francisco, California). Mucolytic agents are drugs belonging to the class of mucoactive medications which are intended to increase the ability to expectorate sputum or to decrease mucus hypersecretion, and these medications are classified based on their proposed method of action. Mucolytic agents degrade polymer gels. Mucolytic agents with N-acetylcysteine being the prototype have free sulfhydryl groups that hydrolyze disulfide bonds of mucins and other proteins.

FIG. 8 is a diagrammatic perspective view of disease detection system 110 that illustrates an embodiment of pretreated-lysed-extracted sputum sample 56 tested using a platform or cartridge and using the method of the present invention based on lateral flow immunoassay (LFIA) when extracting a collected sputum sample in a tube containing a detergent solution and a free-solution proteolytic enzyme Alcalase. The collected sputum sample was incubated for about 15-minutes at room temperature after collection. The incubation mixture of the collected sputum sample was kept gently in motion during the incubation to form pretreated-lysed-extracted sputum sample 56. Drops of pretreated-lysed-extracted sputum sample 56 were applied to sample application pad 12, being formed as a well. About 2 milliliters of sputum, about 1 milliliter of 1% Triton X-100, and about 30 microliter food-grade Alcalase were used. As indicated in FIG. 8, a reading of appearance of band 15 as a Control band appeared in color and Band 17 as a Test band appeared in color. The test resulted positive for the detection of SARS-COV-2 virus, using pretreated-lysed-extracted sputum sample 56. The T band 17 was weaker and thinner, apparently due to the short incubation time, or other factors, for maximum binding between the antigen and the corresponding antibody.

FIG. 9 is a diagrammatic perspective view of disease detection system 120 that illustrates an embodiment of pretreated-lysed-extracted sputum sample 58 tested using a platform or cartridge and using the modified method of the present invention based on lateral flow immunoassay (LFIA). The collected sputum sample was extracted by pre-treating a sample of collected sputum in a tube containing a detergent solution and a free-solution of proteolytic enzyme Alcalase, such as is shown in FIG. 7A, followed by incubation for about one hour at room temperature. The incubation mixture was kept gently in motion during the incubation to form pretreated-lysed-extracted sputum sample 58. Drops of pretreated-lysed-extracted sputum sample 58 were applied to sample application pad 12, being formed as a well. About 2 milliliters of sputum and about 1 milliliter of 1% Triton X-100, and about 30 microliter food-grade Alcalase were used. As indicated in FIG. 9, a reading of appearance of band 15 as a Control band appeared in color and band 17 as a Test band appeared in color. The test resulted positive for the detection of SARS-CoV-2 virus, using pretreated-lysed-extracted sputum sample 58. As demonstrated in this experiment, a longer incubation of the complex macromolecular-composed sputum with the enzyme Alcalase was needed to reach optimal binding conditions. The complexity of each sputum sample in each person is different, depending on if the person is normal or is affected by some respiratory disease. The complexity of each sputum derived from different people with different diseases is different in each disease. Optimization of pretreatment conditions of the sputum using an appropriate concentration of reagents, time of incubation, and temperature may be necessary in certain thick rubbery gel-like type of complex sputum and the amount of viral load present in the sputum.

FIG. 10 is a diagrammatic perspective view of disease detection system 130 that illustrates an embodiment of pretreated-lysed-extracted swab sample 60 tested using a platform or cartridge and employing the modified method of the present invention based on lateral flow immunoassay (LFIA). A swab sample was obtained from the nostrils or external openings of the nasal cavity. The swab sample was pretreated in a tube containing a detergent solution and a free-solution proteolytic of enzyme Alcalase, such as is shown in FIG. 7A, followed by incubation for about one hour at room temperature. The incubation mixture was kept gently in motion during the incubation to form pretreated-lysed-extracted swab sample 60. Drops of pretreated-lysedextracted swab sample 60 from a tube containing pretreated-lysed-extracted swab sample 60 were applied to sample application pad 12, being formed as a well. As indicated in FIG. 10, a reading of the appearance of band 15 as a Control band appeared in color and band 17 as a Test band did not appear in color. The test resulted negative for the detection of SARS-COV-2 virus, using pretreated-lysed-extracted swab sample 60. Identical experiments were performed for sample extractions derived from oropharyngeal, buccal, saliva, mouth washing, and gargle samples. A reading of the appearance of band 15 as a Control band appeared in color and band 17 as a Test band did not appear in color for all these experiments of sample extractions and yielded negative results for the detection of SARS-COV-2 virus, showing a similar profile depicted in FIG. 10 for the pretreated-lysed-extracted swab sample. It is considered that either there was very little amount of virus quantity not able to be detected by the colorimetric test with the rapid lateral flow immunoassay of the method of the present invention or there was not any virus at all.

FIG. 11 is a diagrammatic perspective view of disease detection system 140 that illustrates an embodiment of pretreated-lysed-extracted sputum sample 62 tested using a platform or cartridge and using the method of the present invention based on lateral flow immunoassay (LFIA). A collected sputum sample was extracted by pre-treating a sample of collected sputum in a tube containing a detergent solution and a free-solution proteolytic of enzyme Alcalase, such as is shown in FIG. 7A, followed by incubation for about two-hours at room temperature. The incubation mixture was kept gently in motion during the incubation to form pretreated-lysed-extracted sputum sample 62. Drops of pretreated-lysed-extracted sputum sample 62 were applied to sample application pad 12, being formed as a well. As indicated in FIG. 11, a reading of appearance of band 15 as a Control band appeared in color and band 17 as a Test band appeared in color. The test resulted positive for the detection of SARS-COV-2 virus, using pretreated-lysed-extracted sputum sample material 62. In this case, there was clear evidence that there was sufficient amount of virus trapped within the complex sputum network, and that the proteolytic enzyme was capable of releasing enough viral material to interact with the corresponding antibodies and yield a positive result for the SARS-COV-2 virus.

FIG. 12 is a diagrammatic perspective view of disease detection system 150 that illustrates an embodiment of pretreated-lysed-extracted sputum sample 64 tested using a platform or cartridge and using the method of the present invention based on lateral flow immunoassay (LFIA). A collected sputum sample was extracted by pre-treating a sample of collected sputum in a tube containing a detergent solution and immobilized proteolytic enzyme Alcalase on free floating beads, such as is shown in FIG. 7B, followed by incubation for about two hours at room temperature (Beads were obtained from Tosoh Bioscience LLC, King of Prussia, Pennsylvania, U.S.A., Dynabeads-Thermo Fisher Scientific, Waltham, Massachusetts, U.S.A., and SiliCycle, Quebec City, Quebec, Canada). The incubation mixture was kept gently in motion during the incubation to form pretreated-lysed-extracted sputum sample 64. Drops of pretreated-lysed-extracted sputum sample 64 were applied to sample application pad 12, being formed as a well. As indicated in FIG. 12, a reading of appearance of band 15 as a Control band appeared in color and band 17 as a Test band appeared in color. The test resulted positive for the detection of SARS-COV-2 virus, using pretreated-lysed-extracted sputum sample 64.

This embodiment has the advantage of eliminating any concern regarding that the use of a proteolytic enzyme, as a free-floating enzyme in solution, can damage antibodies present in the lateral flow immunoassay platform or cassette, and therefore, the binding of the corresponding affinity ligand can be affected yielding a false result. The immobilization of the proteolytic enzyme(s) to beads or an internal surface of a tube has an advantage of enabling more reproducible data. The high-binding capacity of polymeric beads or magnetic beads, having a large surface area, can harbor a large quantity of digestive enzyme and the time of sample pre-treatment-lysis-extraction of the sputum can be diminished substantially. In one embodiment, the detection of viral particles and/or their constituents can be achieved in less than 15 minutes using a lateral flow immunoassay test. This screening point-of-care, or point-of-need, modified method may be of great utility when compared to the polymerase chain reaction method, yielding accurate, sensitive, inexpensive, and rapid. Additionally, the immobilized digestive enzymes can be re-used multiple times without carry over after washing them for reducing manufacturing costs and making even more inexpensive the test.

An attempt was made to use ultrasound to disrupt the complex sputum in a lysis buffer having 1% Triton X-100, 8M urea, and 1% protease inhibitor cocktail. The disrupted complex was centrifuged, and the supernatant was subjected to either trypsin or Alcalase, or a combination of both, after reduction with dithiothreitol (DTT) or beta-mercaptoethanol, and alkylated with 15 mM iodoacetamide. It is believed that some minor excess of DTT or beta-mercaptoethanol, and/or free-solution proteolytic enzyme(s) affected integrity of the immunoglobulins present in the platform or cassette of the lateral flow immunoassay system. In consequence, the data was not easy to interpret since the appearance of band 15 as a Control band had less color intensity than band 17 as a Test band and changed from test to test (data not shown). The inconsistency of the results using this lysis buffer with urea and dithiothreitol or beta-mercaptoethanol, confirm the modified method of the present invention is advantageous to obtain reproducible results. It has been found that the more an enzyme, such as Alcalase, is attached to surfaces of particles 40 in tube 38 as shown in FIG. 7B or inner surface 45 of tube 42, as shown in FIGS. 7D, the less time is required to disrupt complex sputum received in tube 38 or tube 42 and liberate its content. Characterization studies were performed using an analytical separation instrument coupled to mass spectrometry which showed the modified method of the present invention yielded cleaner peptides released from the sputum under study, a less cumbersome protocol, and a cost-effective method (not shown). This modified method capable of pretreatment-lysing-extracting the content of sputum, has significant potential to study the sputome or proteome of sputum.

For the purpose of detecting the SARS-COV-2 virus and its constituents using a platform or cartridge and using the method of the present invention based on lateral flow immunoassay (LFIA), the present invention can be carried out as a home test, with minimal training and equipment. The immobilization of the proteolytic enzyme(s) to beads or an internal surface of a tube has is advantageous to diminish any possible toxicity of the proteolytic enzyme in solution. Particularly, when a platform or cartridge and using the modified method of the present invention based on lateral flow immunoassay (LFIA) is used as a kit for assaying the presence of the SARS-CoV-2 virus at home. The immobilized digestive enzymes do not interfere in any possible digestion to the antibodies present in the LFIA platform or cartridge, because the pretreated-lysed-extracted biological sample does not contain any free-digestive enzyme when applied into the sample well of the LFIA platform.

FIG. 13 is a diagrammatic perspective view of disease detection system 160 that illustrates an embodiment of pretreated-lysed-extracted sputum sample 66 tested using a platform or cartridge and employing the modified method of the present invention based on lateral flow immunoassay (LFIA). A collected sputum sample was extracted by pre-treating a sample of collected sputum in a tube containing a detergent solution and a free-solution proteolytic enzyme Alcalase, hyaluronidase, and amylase, such as is shown in FIG. 7A, followed by incubation for about two hours at room temperature. The incubation mixture was kept gently in motion during the incubation to form pretreated-lysed-extracted sputum sample 66. Drops of pretreated-lysed-extracted sputum sample 66 were applied to sample application pad 12, being formed as a well. As indicated in FIG. 13, a reading of appearance of band 15 as a Control band appeared in color and band 17 as a Test band appeared in color. The test resulted positive for the detection of SARS-CoV-2 virus, using pretreated-lysed-extracted sputum sample 56. It is considered that the carbohydrate digesting enzymes hyaluronidase and amylase may be partial contributors of the disruption of the sputum complex network when working separately and independently (data not shown because of its irreproducibility), it is believed that the major disruptor of sputum is the proteolytic enzyme Alcalase, as is shown in FIG. 13.

FIG. 14 is a graphical plot that illustrates the results of a time experiment when performing a rapid test using a platform or cartridge and using the method of the present invention based on lateral flow immunoassay (LFIA) for a sputum sample collected separately and independently, each week for 12 weeks. The results obtained during this time-period shows a positive test for the presence of SARS-COV-2 virus, when pre-treating the sample with a detergent-containing solution and a proteolytic enzyme Alcalase followed by incubation for 2-hours at room temperature. The intensity of a color of band 17 as a Test band, on weekly collected sputum samples, diminishes as time progressed in the time period. Band 15 as a Control band maintained its color intensity over the time period. Although less than one hour incubation time is required to observe the T band 17, when there is enough viral load, incubation of 2 hours was used uniformly during several weeks, just to make sure that when very load viral load was present in the sputum sample, the method was still useful for disrupting the complex meshwork sputum specimen and be able to visualize the small amount of virus that may remain in the sample.

It was found from all experiments that the use of proteolytic enzymes in the method of the present invention, particularly Alcalase, is capable of exposing hidden or antigenic sites of viral specimens present in sputum when using a home-based COVID-19 rapid lateral flow immunoassay test. It was found working with complex sputum is difficult because of the gel-like nature of the sample. When applying the sputum sample directly to sample application pad 12, being formed as a well, of the platform or cassette of the rapid lateral flow immunoassay kit test 10, it does not work very well because the sputum gets stuck in the well of the platform and migration is very poor or not existing. Consequently, the results are inconclusive. It has been found that the modified method has many advantages to test sputum in systems of the present invention using the method of the present invention including disrupting the complex sputum meshwork.

In one embodiment, a qualitative detection of the analyte of interest complex in migration membrane pad 16 is measured by using a chromogenic reagent with the binding molecule of an antibody generating fluorescence, bioluminescence, or chemiluminescence when the binding molecule interacts to bind with the analyte of interest of an antigen and the fluorescence, bioluminescence, or chemiluminescence is detected with a corresponding detector. The detector can be a portable miniaturized instrument.

In one embodiment a signal is detectable at band 15 as a Control band or band 17 as a Test band where the signal is a colorimetric signal. The colorimetric signal is detectable if visible with the naked eye or detected using a reader device for the lateral flow immunoassay (LFIA). In one embodiment a signal is detectable at band 15 as a Control band or band 17 as a Test band where the signal is fluorescent signal, bioluminescent signal or chemiluminescent signal which are detectable if visible with the naked eye or detected using a reader device for the lateral flow immunoassay (LFIA). The processing of data generated by systems 100, 110, 120, 130, 140 and 150 including colorimetric signals, fluorescent signals, bioluminescent signals, and chemiluminescent signals can be controlled by a central processing unit (CPU) capable of organizing and storing results and the data. The data can be calibrated against various concentrations of standards. The data can be sent via the Internet to a healthcare specialist for interpretation of the data. The data can be sent via the Internet to a specialized laboratory. The specialized laboratory performing analysis for determining further information, such for example identification of released peptides by analytical separation techniques coupled to solid-phase affinity extraction methods and mass spectrometry, providing qualitative and quantitative information.

In one embodiment, a kit is formed of disease detection system 100, 110, 120, 130, 140 or 150 with a tube or container 36, 38, 42, 46 and 52 and optionally transfer component 54. In one embodiment, a kit includes digestive enzyme 44 and at least one detergent within tube or container 36, 38, 42, 46 and 52. Digestive enzyme 44 is free-floating within tube or container 36. In one embodiment, a kit includes digestive enzyme 44 immobilized to inner wall 45 of tube or container 42 and including at least one detergent contained within tube or container 42. In one embodiment, a kit includes digestive enzyme 44 immobilized to particles 40 within tube or container 38 and at least one detergent contained within tube or container 38. In one embodiment, a kit includes magnetic beads 48 containing immobilized digestive enzyme 44 to surfaces of magnetic beads 48 within tube or container 52, magnet support 50 and at least one detergent contained within tube or container 52. Digestive enzyme 44 used in embodiments of the kit can be a proteolytic enzyme, such as Alcalase.

In one embodiment a kit is formed of disease detection system 100, 110, 120, 130, 140 or 150 with a tube or container 36, 38 or 42 and optionally transfer component 54 for receiving a sample from sputum, blood, serum, plasma, synovial fluid, lavage fluids, vaginal or urethral secretions, tissue biopsies, cerebrospinal fluid, amniotic fluid, urine, tears, sweat or transdermal exudates skin, nails, feces, hair, and hair follicles. Digestive enzyme 44 used in embodiments of the kit can be used in solution with at least one detergent. Digestive enzyme 44 used in embodiments of the kit can be a proteolytic enzyme, such as Alcalase.

A rapid test using a platform or cartridge and using the method of the present invention based on lateral flow immunoassay (LFIA) can be used as an alternative test to determine how long the SARS-COV-2 can be detected in sputum, at a significant low cost per assay.

Mild or moderate COVID-19 lasts about two weeks for most people, but others experience lingering health problems even after the fever and cough go away and they are no longer testing positive for the illness. These individuals are often referred as "COVID long-haulers" and have post-COVID conditions or "long COVID" Raveendran et al., *Diabetes & Metabolic Syndrome: Clinical Research & Reviews* 2021, volume 15, pages 869-875; doi:10.1016/j.dsx.2021.04.007].

As the numbers grow, COVID-19 "long haulers" stump experts [Rubin, *Journal of the Americal Medical Association* 2020, volume 324, issue 14, pages 1381-1383; Marshall, *Nature* 2020, volume 585, pages 339-341; doi: 10.1038/d41586-020-02598-6; Schmidt, *Nature Biotechnology* 2021, volume 39, pages 908-913; doi: 101038/s41587-021-00984-7; Sansone et al., *Sexual Medicine Reviews* 2022, volume 10, pages 271-285; doi:10.1016/j.sxmr.2021.11.001; Ramakrishnan et al., *Frontiers in Immunology* 2021, volume 12: 686029; doi:10.3389/fimmu.2021.686029]. Recently, it has been reported that persistent circulating SARS-CoV-2 spike is associated with post-acute COVID-19 sequelae.

It is known that long-hauler COVID-19 patients have symptoms and severities that vary enormously. There are no precise statistics on the number of long hauler patients. It is known that SARS-COV-2 viral RNA is still present in feces of more than 60% of patients, after pharyngeal swab testing turned negative suggesting that fecal-oral transmission may serve as an alternative route for SARS-COV-2 transmission. The viral RNA testing for SARS-COV-2 was determined by the real-time reverse transcription-polymerase chain reaction (RT-PCR), and the assay was conducted in accordance with the protocol established by the World Health Organization [Chen et al., *Journal of Medical Biology* 2020, volume 92, pages 833-840; doi: 10.1002/jmv.25825].

One patient with COVID-19 was still positive for the SARS-COV-2 viral testing after 111 days, when assaying for the presence of RNA in nasopharyngeal specimens using the sensitive quantitative reverse transcriptase-polymerase chain reaction (qRT-PCR) technique [Abe et al., *QJM-International Journal of Medicine* 2021; volume 114, issue 1, pages 47-49; doi:10.1093/qjmed/hcaa296]. A rapid test using a platform or cartridge and using the modified method of the present invention based on lateral flow immunoassay (LFIA) showed a positive reaction of color for band 17 as a Test band using sputum samples for more than 3 months of testing, but no color was observed for band 17 as a Test band when using nasopharyngeal or oropharyngeal samples. The intensity of the color of band 17 as a Test band diminished gradually during the 3 months of testing. The patient had no symptoms during this time except lasting cough. Patients with ongoing symptoms of COVID-19, long-haulers, could be chronically infected with COVID-19, but apparently not able to transmit the disease. The modified method of the present invention may have the advantage to elucidate the mystery surrounding post-acute sequelae of COVID-19.

Although a rapid test using a platform or cartridge and using the method of the present invention based on lateral flow immunoassay (LFIA) has less analytical sensitivity, for detecting the SARS-COV-2 viral protein, than the conventional quantitative reverse transcriptase polymerase chain reaction (qRT-PCR) method reported by other laboratories, for detecting viral RNA, in nasopharyngeal and oropharyngeal samples, it has been found that detection of the viral protein in sputum can still be visualized for a three-month period. The conventional qRT-PCR method has the disadvantages of being tedious, time consuming, expensive, requiring expertise, and must be performed in a laboratory. It has been found that the information contained within the transcriptome is intrinsically flexible and variant. If this variability is combined with the technical limitations inherent in any reverse-transcription polymerase chain reaction (RT-PCR), it can be difficult to achieve not just technically accurate but biologically relevant results. Pitfalls on the RT-PCR have been reported [Bustin et al., *Journal of Biomolecular Techniques* 2004, volume 15, issue 3, pages 155-166]. The rapid test using a platform or cartridge and using the method of the present invention based on lateral flow immunoassay (LFIA) the color-visual method described has the advantages of being very simple, requiring no expertise, is inexpensive, and can be performed at home.

A rapid test using a platform or cartridge system of the present invention and using the modified method of the present invention based on lateral flow immunoassay (LFIA) has multiple applications. For example, it can be used for the determination of other viruses and/or bacteria, or any pathogenic microbial or toxicological entity trapped on and release from the complex sputum meshwork. It can also be used for the determination of several substances present in other biosamples, such as blood, urine, feces, lavage fluids, or extracts of cells. It can determine antigens and/or antibodies molecular entities, in addition to a wide range of molecules. It can be a very useful pretreatment method to be combined with analytical separation technologies and mass spectrometry. For routine testing of SARS-COV-2 virus and other pathogens, rapid test using a platform or cartridge system of the present invention and using the method of the present invention based on lateral flow immunoassay (LFIA) can be a viable alternative to the gold-standard RT-PCR method. With large quantities of immobilized proteolytic enzyme Alcalase to beads and/or the inner surface of a tube, the disruption of the sputum and release of viral components can happen in a few minutes, making the method of the present invention capable of rapid testing for the presence of a virus and capable of yielding accurate results.

In addition to applications in disease diagnosis, the modified method of the present invention can have an impact on the fields of food safety, and environmental monitoring. Significant benefits can be obtained as a cost-effective point-of-care device for use in resource-limited areas such as developing countries and rural areas.

It is to be understood that the above-described method and system to disrupt sputum capable to detect released pathogens and/or its constituent components, and to study the sputum, can have numerous and varied modifications that can be readily devised in accordance with the principles described in this patent by those skilled in the art without departing from the spirit and scope of the invention.

What is claimed is:

1. A disease detection system, comprising:
   a platform or cartridge configured to perform a rapid lateral flow chromatographic immunoassay (LFIA) test;
   a container or tube configured for receiving a sample;
   a detergent contained in the container or tube, the detergent comprising one or more non-ionic detergents;
   a digestive enzyme, the digestive enzyme is in solution with the detergent contained in the container or tube or the digestive enzyme is immobilized on a solid support, the solid support being a surface of a particle within the container or tube or the solid support being an inner surface of the container or tube, the digestive enzyme is one or more of subtilisin, trypsin, pepsin, chymotrypsin, pronase, papain, proteinase K, thermophilic enzyme, hyaluronidase, and amylase;

a sample application zone disposed on or in the platform or cartridge configured for receiving the sample, the sample having been disrupted by the digestive enzyme and the detergent contained in the container or tube to release content and digest proteins and glycoproteins of the sample to form a lysed-digested-extracted sample; and a migration zone disposed on the platform or cartridge receiving flow of the lysed-digested-extracted sample from the sample application zone by capillary action, the migration zone including a binding molecule to bind with an analyte of interest to generate an analyte of interest complex, wherein qualitative detection of the analyte of interest complex in the migration zone indicates presence of the analyte of interest in the lysed-digested-extracted sample and wherein the analyte of interest is a nucleocapsid protein antigen from SARS-CoV-2 and wherein when the digestive enzyme is one or more digestive enzymes in a solution with the detergent, the one or more digestive enzymes being in an amount ranging from about 0.1% to about 10% of total volume of the sample and the one or more detergents being in an amount ranging from about 0.1% to about 2% of total volume of the sample.

2. The disease detection system of claim 1 wherein the sample is from collected sputum, blood, serum, plasma, synovial fluid, lavage fluids, vaginal or urethral secretions, tissue biopsies, cerebrospinal fluid, amniotic fluid, urine, tears, sweat or transdermal exudates skin, nails, feces, hair, or hair follicles and wherein the binding molecule is an antibody, the analyte of interest complex is an antigen-antibody complex.

3. The disease detection system of claim 1 wherein the digestive enzyme is subtilisin.

4. The disease detection system of claim 1 wherein the particle is a bead formed of glass, a polymeric material or a mixture of glass and a polymeric material.

5. A disease detection system, comprising:
a platform or cartridge configured to perform a rapid lateral flow chromatographic immunoassay (LFIA) test;
a container or tube configured for receiving a sample;
a detergent contained in the container or tube, the detergent comprising one or more non-ionic detergents;
a digestive enzyme, the digestive enzyme is in solution with the detergent contained in the container or tube or the digestive enzyme is immobilized on a solid support, the solid support being a surface of a particle within the container or tube or the solid support being an inner surface of the container or tube, the digestive enzyme is one or more of subtilisin, trypsin, pepsin, chymotrypsin, pronase, papain, proteinase K, thermophilic enzyme, hyaluronidase, and amylase;
a sample application zone disposed on or in the platform or cartridge configured for receiving the sample, the sample having been disrupted by the digestive enzyme and the detergent contained in the container or tube to release content and digest proteins and glycoproteins of the sample to form a lysed-digested-extracted sample; and
a migration zone disposed on the platform or cartridge receiving flow of the lysed-digested-extracted sample from the sample application zone by capillary action, the migration zone including a binding molecule to bind with an analyte of interest to generate an analyte of interest complex,
wherein qualitative detection of the analyte of interest complex in the migration zone indicates presence of the analyte of interest in the lysed-digested-extracted sample and wherein the qualitative detection of the analyte of interest complex in the migration zone is measured by formation of a color when the binding molecule conjugated with a color indicator interacts to bind with the analyte of interest and generate a characteristic color and wherein the analyte of interest is a nucleocapsid protein antigen from SARS-CoV-2 and wherein when the digestive enzyme is one or more digestive enzymes in a solution with the detergent, the one or more digestive enzymes being in an amount ranging from about 0.1% to about 10% of total volume of the sample and the one or more detergents being in an amount ranging from about 0.1% to about 2% of total volume of the sample.

6. The disease detection system of claim 1 wherein the qualitative detection of the analyte of interest complex in the migration zone is a colorimetric signal generated when the binding molecule interacts to bind with the analyte of interest, the colorimetric signal being detectable if visible with the naked eye or being measured by a detector and being processed at a central processing unit (CPU) configured to organize and store results and data directed to the colorimetric signal, the central processing unit (CPU) configured to calibrate the data against standards and the central processing unit (CPU) configured to send the data via to a healthcare specialist for interpretation of the data or to a specialized laboratory for performing analysis of the data.

7. A disease detection system, comprising:
a platform or cartridge configured to perform a rapid lateral flow chromatographic immunoassay (LFIA) test;
a container or tube configured for receiving a sample;
a detergent contained in the container or tube, the detergent comprising one or more non-ionic detergents;
a digestive enzyme, the digestive enzyme is in solution with the detergent contained in the container or tube or the digestive enzyme is immobilized on a solid support, the solid support being a surface of a particle within the container or tube or the solid support being an inner surface of the container or tube, the digestive enzyme is one or more of subtilisin, trypsin, pepsin, chymotrypsin, pronase, papain, proteinase K, thermophilic enzyme, hyaluronidase, and amylase;
a sample application zone disposed on or in the platform or cartridge configured for receiving the sample, the sample having been disrupted by the digestive enzyme and the detergent contained in the container or tube to release content and digest proteins and glycoproteins of the sample to form a lysed-digested-extracted sample; and
a migration zone disposed on the platform or cartridge receiving flow of the lysed-digested-extracted sample from the sample application zone by capillary action, the migration zone including a binding molecule to bind with an analyte of interest to generate an analyte of interest complex,
wherein qualitative detection of the analyte of interest complex in the migration zone indicates presence of the analyte of interest in the lysed-digested-extracted sample and wherein the qualitative detection of the analyte of interest complex in the migration zone is measured by using a chromogenic reagent with the binding molecule generating fluorescence, bioluminescence, or chemiluminescence when the binding molecule interacts to bind with the analyte of interest and the fluorescence, bioluminescence, or chemiluminescence is detected with a detector and wherein when the digestive enzyme is one or more digestive enzymes in a solution with the detergent, the one or more digestive enzymes being in an amount ranging from about 0.1% to about 10% of total volume of the sample and the one or more detergents being in an amount ranging from about 0.1% to about 2% of total volume of the sample; and wherein the analyte of interest is a protein.

8. The disease detection system of claim 1 wherein the qualitative detection of the analyte of interest complex in the migration zone is a signal of one or more of a colorimetric signal, fluorescent signal, bioluminescent signal or chemiluminescent signal generated when the binding molecule interacts to bind with the analyte of interest, the signal being detectable if visible with the naked eye or being measured by a detector and information of the qualitative detection and quantitative data being processed at a central processing unit (CPU) configured to organize and store results and data directed to the signal, the central processing unit (CPU) configured to calibrate the data against standards and the central processing unit (CPU) configured to send the data via internet to a healthcare specialist for interpretation of the data or to a specialized laboratory for performing analysis of the data.

* * * * *